US008507672B2

(12) United States Patent
Harrison et al.

(10) Patent No.: US 8,507,672 B2
(45) Date of Patent: Aug. 13, 2013

(54) SUBSTITUTED PYRROLO[2,3-D]PYRIMIDINES AS LIM KINASE 2 INHIBITORS

(75) Inventors: Bryce Alden Harrison, Hamilton, NJ (US); Spencer David Kimball, East Windsor, NJ (US); Ross Mabon, Princeton, NJ (US); David Brent Rawlins, Morrisville, PA (US); Dennis S. Rice, The Woodlands, TX (US); Michael Victor Voronkov, Pennington, NJ (US); Yulian Zhang, Yardley, PA (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 1002 days.

(21) Appl. No.: 12/188,515

(22) Filed: Aug. 8, 2008

(65) Prior Publication Data

US 2009/0042893 A1    Feb. 12, 2009

Related U.S. Application Data

(60) Provisional application No. 60/954,698, filed on Aug. 8, 2007.

(51) Int. Cl.
*C07D 487/04* (2006.01)
*A61K 31/519* (2006.01)
*A61K 31/4985* (2006.01)
*A61P 29/00* (2006.01)
*A61P 35/00* (2006.01)

(52) U.S. Cl.
USPC ............... 544/280; 514/252.16; 514/249

(58) Field of Classification Search
USPC ............. 544/280; 514/265.1, 249, 252.16
See application file for complete search history.

(56) References Cited

U.S. PATENT DOCUMENTS

2005/0130954 A1 * 6/2005 Mitchell et al. .......... 514/210.21
2008/0076924 A1 * 3/2008 Betschmann et al. ........ 544/279

OTHER PUBLICATIONS

International Search Report for Corresponding Patent Application No. PCT/US2008/072584, filed Aug. 8, 2008.

* cited by examiner

*Primary Examiner* — Susanna Moore
(74) *Attorney, Agent, or Firm* — Max Bachrach

(57) ABSTRACT

Substituted pyrrolo[2,3-d]pyrimidine-based compounds useful as inhibitors of LIM kinase 2 are disclosed. Also disclosed are pharmaceutical compositions comprising the compounds and methods of their use to treat, manage and prevent inflammatory diseases and disorders, cancer, and diseases and disorders of the eye.

12 Claims, 2 Drawing Sheets

SUBSTITUTED PYRROLO[2,3-D]PYRIMIDINES AS LIM KINASE 2 INHIBITORS

Figure 1:
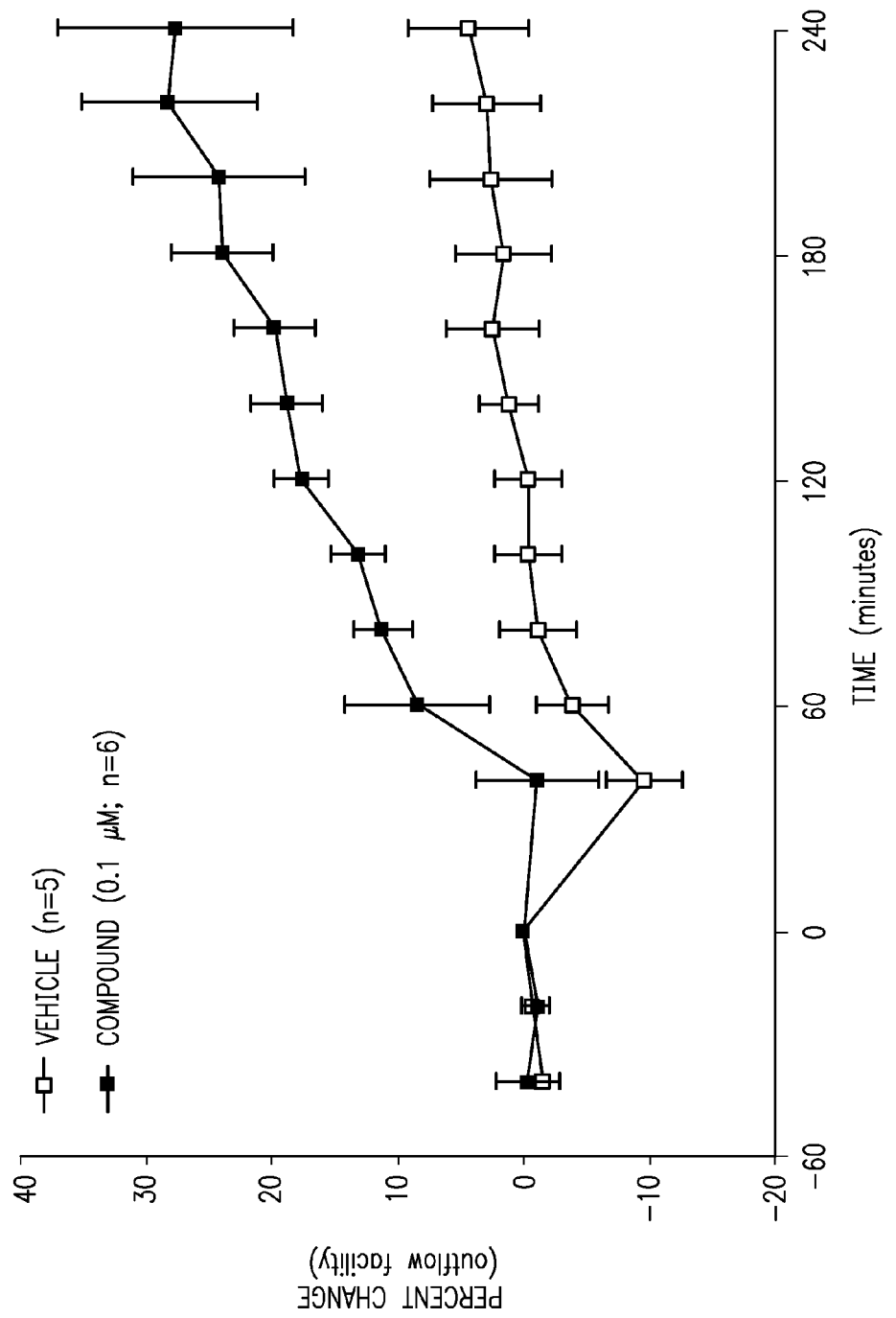

This application claims priority to U.S. provisional application No. 60/954,698, filed Aug. 8, 2007, the entirety of which is incorporated herein by reference.

1. FIELD OF THE INVENTION

This invention relates to kinase inhibitors, compositions comprising them, and methods of their use to treat various diseases and disorders.

2. BACKGROUND

Protein kinases are a class of enzymes that catalyze the transfer of the γ-phosphate group from ATP to a recipient protein. The human genome is estimated to encode in excess of 500 distinct protein kinases, of which many have been implicated in a wide range of diseases and disorders, including cancer and inflammation.

The LIM kinases (LIMK) have been linked to the p53 pathway. See, e.g., International Application No. WO 02/099048. LIMK belongs to a small subfamily of kinases with a unique combination of two N-terminal LIM motifs and a C-terminal protein kinase domain. These LIM motifs and kinase domains are linked by a proline- and serine-rich region containing several putative casein kinase and map kinase recognition sites. LIM kinases and their pathway proteins are believed to contribute to Rho-induced reorganization of the actin cytoskeleton. Id. Members of the LIM kinase family include LIM kinase 1 (LIMK1) and LIM kinase 2 (LIMK2). Both phosphorylate cofilin and regulates Rho family-dependent actin cytoskeletal rearrangement. Id.

LIM kinase inhibitors have been proposed for the treatment of cancer. Id. It has also been suggested that LIMK inhibitors may be useful in treating glaucoma, by promoting actin depolymerization in trabecular cells and lowering ocular tension. See International Application No. WO 04/047868.

An enormous number of compounds, with a wide variety of chemotypes, have been reported as kinase inhibitors. For example, phenyl-substituted pyrimidine compounds have been disclosed that are reportedly useful as LIMK inhibitors. See International Application WO 2006/084017. Pyrrole[2,3-d]pyrimidine-based compounds have been disclosed as Janus Kinase 3 inhibitors. See, e.g., U.S. patent publication no. 2004/0058922. Some pyrrole[2,3-d]pyrimidine-based have also been disclosed among a wide variety of other compounds as potential AKT protein kinase inhibitors. See U.S. patent publication no. 2005/0130954. Some pyrrole[2,3-d]pyrimidine-based kinase inhibitors are reportedly useful in the treatment of cancer. See U.S. patent application Ser. No. 11/354,636, filed Feb. 15, 2006.

3. SUMMARY OF THE INVENTION

This invention is directed, in part, to compounds of formulae I and II:

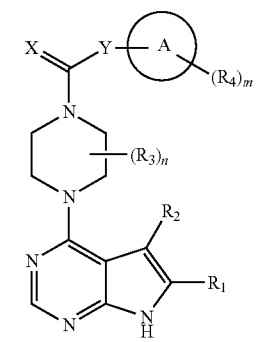

I

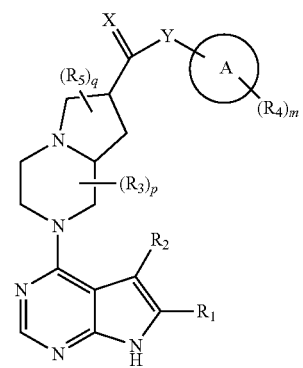

II and pharmaceutically acceptable salts thereof, the substituents of which are defined herein. Particular compounds of these formulae are potent inhibitors of LIMK2.

One embodiment of the invention encompasses pharmaceutical formations comprising compounds disclosed herein (e.g., compounds of formulae I and II).

Another embodiment encompasses methods of using the compounds disclosed herein for the treatment, management and prevention of various diseases and disorders affected by LIMK2, including cancer, inflammatory diseases and disorders, and disease and disorders affecting vision (e.g., diseases and disorders of the eye), such as glaucoma, neurodegeneration and infection.

4. BRIEF DESCRIPTION OF THE FIGURES

FIG. 1 shows the effect of a compound of the invention in the pig anterior chamber organ culture perfusion assay described in the Examples below. Here, a 0.1 μM solution containing a compound of the invention was found to increase the outflow as a function of time.

Figure 2:
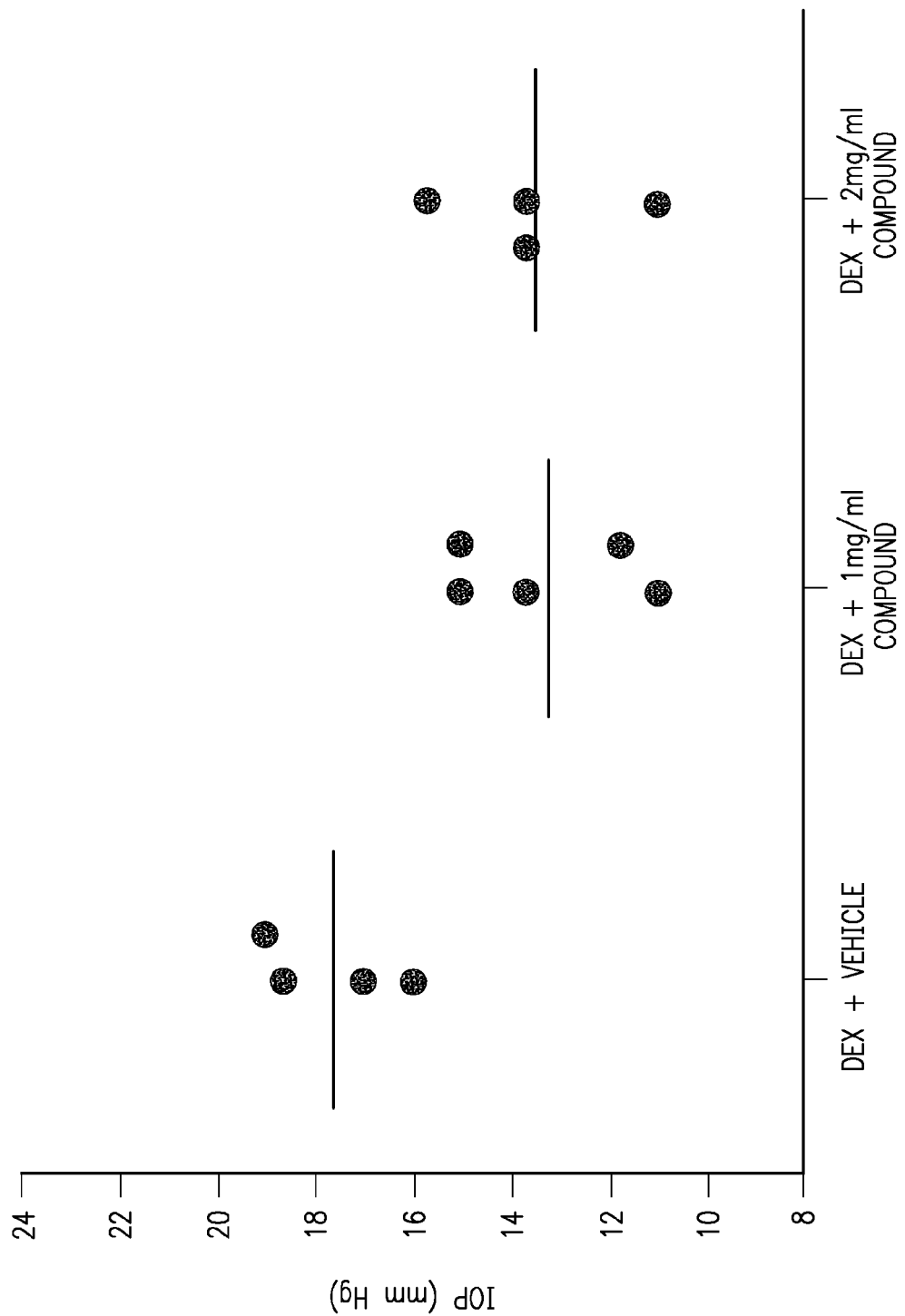

FIG. 2 shows the effect of a compound of the invention in the ocular hypertensive model described in the Examples below. Female F2 wild-type mice were used. The data in this figure were obtained one hour after topical application of the compound to the eyes of the mice.

5. DETAILED DESCRIPTION

This invention is based, in part, on the discovery of novel inhibitors of LIM kinase 2 (LIMK2), which may be used to treat, manage and/or prevent a variety of diseases and disorders.

5.1. Definitions

Unless otherwise indicated, the term "alkenyl" means a straight chain, branched and/or cyclic hydrocarbon having from 2 to 20 (e.g., 2 to 10 or 2 to 6) carbon atoms, and including at least one carbon-carbon double bond. Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl.

Unless otherwise indicated, the term "alkoxy" means an —O-alkyl group. Examples of alkoxy groups include, but are not limited to, —OCH$_3$, —OCH$_2$CH$_3$, —O(CH$_2$)$_2$CH$_3$, —O(CH$_2$)$_3$CH$_3$, —O(CH$_2$)$_4$CH$_3$, and —O(CH$_2$)$_5$CH$_3$.

Unless otherwise indicated, the term "alkyl" means a straight chain, branched and/or cyclic ("cycloalkyl") hydrocarbon having from 1 to 20 (e.g., 1 to 10 or 1 to 4) carbon atoms. Alkyl moieties having from 1 to 4 carbons are referred to as "lower alkyl." Examples of alkyl groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). The term "alkyl" includes saturated hydrocarbons as well as alkenyl and alkynyl moieties.

Unless otherwise indicated, the term "alkylaryl" or "alkyl-aryl" means an alkyl moiety bound to an aryl moiety.

Unless otherwise indicated, the term "alkylheteroaryl" or "alkyl-heteroaryl" means an alkyl moiety bound to a heteroaryl moiety.

Unless otherwise indicated, the term "alkylheterocycle" or "alkyl-heterocycle" means an alkyl moiety bound to a heterocycle moiety.

Unless otherwise indicated, the term "alkynyl" means a straight chain, branched or cyclic hydrocarbon having from 2 to 20 (e.g., 2 to 20 or 2 to 6) carbon atoms, and including at least one carbon-carbon triple bond. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl.

Unless otherwise indicated, the term "aryl" means an aromatic ring or an aromatic or partially aromatic ring system composed of carbon and hydrogen atoms. An aryl moiety may comprise multiple rings bound or fused together. Examples of aryl moieties include, but are not limited to, anthracenyl, azulenyl, biphenyl, fluorenyl, indan, indenyl, naphthyl, phenanthrenyl, phenyl, and 1,2,3,4-tetrahydronaphthalene.

Unless otherwise indicated, the term "arylalkyl" or "aryl-alkyl" means an aryl moiety bound to an alkyl moiety.

Unless otherwise indicated, the terms "halogen" and "halo" encompass fluorine, chlorine, bromine, and iodine.

Unless otherwise indicated, the term "heteroalkyl" refers to an alkyl moiety (e.g., linear, branched or cyclic) in which at least one of its carbon atoms has been replaced with a heteroatom (e.g., N, O or S).

Unless otherwise indicated, the term "heteroaryl" means an aryl moiety wherein at least one of its carbon atoms has been replaced with a heteroatom (e.g., N, O or S). Examples include, but are not limited to, acridinyl, benzimidazolyl, benzofuranyl, benzoisothiazolyl, benzoisoxazolyl, benzoquinazolinyl, benzothiazolyl, benzoxazolyl, furyl, imidazolyl, indolyl, isothiazolyl, isoxazolyl, oxadiazolyl, oxazolyl, phthalazinyl, pyrazinyl, pyrazolyl, pyridazinyl, pyridyl, pyrimidinyl, pyrimidyl, pyrrolyl, quinazolinyl, quinolinyl, tetrazolyl, thiazolyl, and triazinyl.

Unless otherwise indicated, the term "heteroarylalkyl" or "heteroaryl-alkyl" means a heteroaryl moiety bound to an alkyl moiety.

Unless otherwise indicated, the term "heterocycle" refers to an aromatic, partially aromatic or non-aromatic monocyclic or polycyclic ring or ring system comprised of carbon, hydrogen and at least one heteroatom (e.g., N, O or S). A heterocycle may comprise multiple (i.e., two or more) rings fused or bound together. Heterocycles include heteroaryls. Examples include, but are not limited to, benzo[1,3]dioxolyl, 2,3-dihydro-benzo[1,4]dioxinyl, cinnolinyl, furanyl, hydantoinyl, morpholinyl, oxetanyl, oxiranyl, piperazinyl, piperidinyl, pyrrolidinonyl, pyrrolidinyl, tetrahydrofuranyl, tetrahydropyranyl, tetrahydropyridinyl, tetrahydropyrimidinyl, tetrahydrothiophenyl, tetrahydrothiopyranyl and valerolactamyl.

Unless otherwise indicated, the term "heterocyclealkyl" or "heterocycle-alkyl" refers to a heterocycle moiety bound to an alkyl moiety.

Unless otherwise indicated, the term "heterocycloalkyl" refers to a non-aromatic heterocycle.

Unless otherwise indicated, the term "heterocycloalkylalkyl" or "heterocycloalkyl-alkyl" refers to a heterocycloalkyl moiety bound to an alkyl moiety.

Unless otherwise indicated, the term "LIMK2 IC$_{50}$" is the IC$_{50}$ of a compound determined using the in vitro human LIM kinase 2 inhibition assay described in the Examples, below.

Unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

Unless otherwise indicated, the term "pharmaceutically acceptable salts" refers to salts prepared from pharmaceutically acceptable non-toxic acids or bases including inorganic acids and bases and organic acids and bases. Suitable pharmaceutically acceptable base addition salts include, but are not limited to, metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art. See, e.g., *Remington's Pharmaceutical Sciences*, 18$^{th}$ ed. (Mack Publishing, Easton Pa.: 1990) and *Remington: *The Science and Practice of Pharmacy*, 19th ed. (Mack Publishing, Easton Pa.: 1995).

Unless otherwise indicated, a "potent LIMK2 inhibitor" is a compound that has a LIMK2 $IC_{50}$ of less than about 250 nM.

Unless otherwise indicated, the terms "prevent," "preventing" and "prevention" contemplate an action that occurs before a patient begins to suffer from the specified disease or disorder, which inhibits or reduces the severity of the disease or disorder. In other words, the terms encompass prophylaxis.

Unless otherwise indicated, a "prophylactically effective amount" of a compound is an amount sufficient to prevent a disease or condition, or one or more symptoms associated with the disease or condition, or prevent its recurrence. A "prophylactically effective amount" of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

Unless otherwise indicated, the term "stereoisomeric mixture" encompasses racemic mixtures as well as stereomerically enriched mixtures (e.g., R/S=30/70, 35/65, 40/60, 45/55, 55/45, 60/40, 65/35 and 70/30).

Unless otherwise indicated, the term "stereomerically pure" means a composition that comprises one stereoisomer of a compound and is substantially free of other stereoisomers of that compound. For example, a stereomerically pure composition of a compound having one stereocenter will be substantially free of the opposite stereoisomer of the compound. A stereomerically pure composition of a compound having two stereocenters will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound.

Unless otherwise indicated, the term "substituted," when used to describe a chemical structure or moiety, refers to a derivative of that structure or moiety wherein one or more of its hydrogen atoms is substituted with a chemical moiety or functional group such as, but not limited to, alcohol, aldehyde, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (e.g. —C(O)NH-alkyl-, -alkyl-NHC(O)alkyl), amidinyl (e.g., —C(NH)NH-alkyl-, —C(NR)NH$_2$), amine (primary, secondary and tertiary such as alkylamino, arylamino, arylalkylamino), aroyl, aryl, aryloxy, azo, carbamoyl (e.g., —NHC(O)O-alkyl-, —OC(O)NH-alkyl), carbamyl (e.g., CONH$_2$, CONH-alkyl, CONH-aryl, CONH-arylalkyl), carbonyl, carboxyl, carboxylic acid, carboxylic acid anhydride, carboxylic acid chloride, cyano, ester, epoxide, ether (e.g., methoxy, ethoxy), guanidino, halo, haloalkyl (e.g., —CCl$_3$, —CF$_3$, —C(CF$_3$)$_3$), heteroalkyl, hemiacetal, imine (primary and secondary), isocyanate, isothiocyanate, ketone, nitrile, nitro, oxo, phosphodiester, sulfide, sulfonamido (e.g., SO$_2$NH$_2$), sulfone, sulfonyl (including alkylsulfonyl, arylsulfonyl and arylalkylsulfonyl), sulfoxide, thiol (e.g., sulfhydryl, thioether) and urea (e.g., —NHCONH-alkyl-).

Unless otherwise indicated, a "therapeutically effective amount" of a compound is an amount sufficient to provide a therapeutic benefit in the treatment or management of a disease or condition, or to delay or minimize one or more symptoms associated with the disease or condition. A "therapeutically effective amount" of a compound means an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, the terms "treat," "treating" and "treatment" contemplate an action that occurs while a patient is suffering from the specified disease or disorder, which reduces the severity of the disease or disorder, or retards or slows the progression of the disease or disorder.

Unless otherwise indicated, the term "include" has the same meaning as "include, but are not limited to," and the term "includes" has the same meaning as "includes, but is not limited to." Similarly, the term "such as" has the same meaning as the term "such as, but not limited to."

Unless otherwise indicated, one or more adjectives immediately preceding a series of nouns is to be construed as applying to each of the nouns. For example, the phrase "optionally substituted alky, aryl, or heteroaryl" has the same meaning as "optionally substituted alky, optionally substituted aryl, or optionally substituted heteroaryl."

Unless otherwise indicated, a structure or name of a compound or genus of compounds encompasses all forms of that compound or genus of compounds, and all compositions comprising that compound or genus of compounds.

It should be noted that a chemical moiety that forms part of a larger compound may be described herein using a name commonly accorded it when it exists as a single molecule or a name commonly accorded its radical. For example, the terms "pyridine" and "pyridyl" are accorded the same meaning when used to describe a moiety attached to other chemical moieties. Thus, the two phrases "XOH, wherein X is pyridyl" and "XOH, wherein X is pyridine" are accorded the same meaning, and encompass the compounds pyridin-2-ol, pyridin-3-ol and pyridin-4-ol.

It should also be noted that if the stereochemistry of a structure or a portion of a structure is not indicated with, for example, bold or dashed lines, the structure or the portion of the structure is to be interpreted as encompassing all stereoisomers of it. Moreover, any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit.

5.2. Compounds

One embodiment of this invention encompasses compounds of formula I:

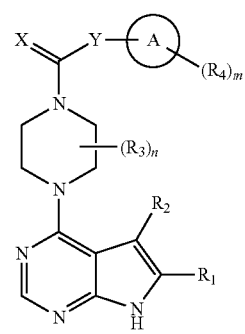

I and pharmaceutically acceptable salts thereof, wherein: X is O or $NR_A$; Y is O, $NR_B$, or $C(R_B)_2$; A is cycloalkyl, aryl or heterocycle; $R_1$ is hydrogen, $OR_B$, $N(R_B)_2$, $SR_B$, or optionally substituted alkyl, aryl, or heterocycle; $R_2$ is hydrogen, halogen, cyano, $OR_B$, $N(R_B)_2$, $SR_B$, or optionally substituted alkyl, aryl, or heterocycle; each $R_3$ is independently halogen or optionally substituted alkyl, and/or two $R_3$s may be taken together with the ring to which they are attached to provide an optionally substituted cycloalkyl or heterocycle; each $R_4$ is cyano, halogen, hydroxy, nitro, $R_C$, $OR_C$, $N(R_C)_2$, $NHC(O)R_C$, $C(O)R_C$, $C(O)N(R_C)_2$, $CSO_2R_C$, $CSO_2N(R_C)_2$, or $SO_2R_C$; $R_A$ is hydrogen, cyano, nitro, $R_{A1}$, $SO_2R_{A1}$, $SO_2NR_{A1}$, or $SO_2N(R_{A1})_2$; each $R_{A1}$ is independently hydrogen or optionally substituted alkyl, heteroalkyl, aryl, heterocycle, alkylaryl, or alkylheterocycle; each $R_B$ is independently hydrogen or optionally substituted alkyl; each $R_C$ is independently hydrogen or optionally substituted alkyl, heteroalkyl, aryl, heterocycle, alkylaryl, or alkylheterocycle; n is 0-8; and m is 0-4.

In a particular embodiment of the invention, when X is O, Y is $C(R_B)_2$, one $R_B$ is hydrogen and the other $R_B$ is substituted alkyl, A is not chlorophenyl or dichlorophenyl. In another, when X is O, Y is not $C(R_B)_2$.

Certain compounds of formula I are of the formula:

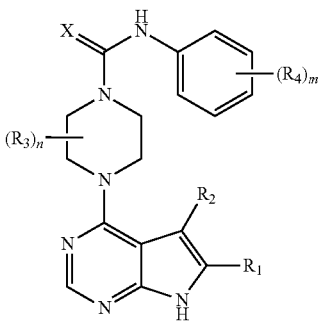

Particular compounds are of the formulae:

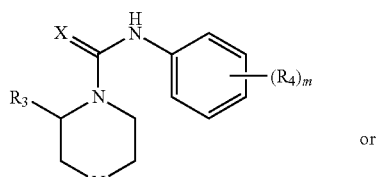

or

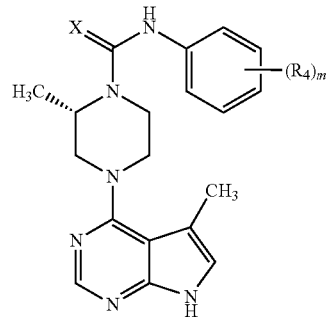

Another embodiment of the invention encompasses compounds of formula II:

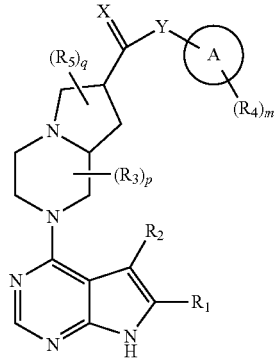

II and pharmaceutically acceptable salts thereof, wherein: X is O or $NR_A$; Y is O, $NR_B$, or $C(R_B)_2$; A is cycloalkyl, aryl or heterocycle; $R_1$ is hydrogen, $OR_B$, $N(R_B)_2$, $SR_B$, or optionally substituted alkyl, aryl, or heterocycle; $R_2$ is hydrogen, halogen, cyano, $OR_B$, $N(R_B)_2$, $SR_B$, or optionally substituted alkyl, aryl, or heterocycle; each $R_3$ is independently halogen or optionally substituted alkyl, and/or two $R_3$s may be taken together with the ring to which they are attached to provide an optionally substituted cycloalkyl or heterocycle; each $R_4$ is cyano, halogen, hydroxy, nitro, $R_C$, $OR_C$, $N(R_C)_2$, $NHC(O)R_C$, $C(O)R_C$, $C(O)N(R_C)_2$, $CSO_2R_C$, $CSO_2N(R_C)_2$, or $SO_2R_C$; $R_A$ is hydrogen, cyano, nitro, $R_{A1}$, $SO_2R_{A1}$, $SO_2NR_{A1}$, or $SO_2N(R_{A1})_2$; each $R_{A1}$ is independently hydrogen or optionally substituted alkyl, heteroalkyl, aryl, heterocycle, alkylaryl, or alkylheterocycle; each $R_B$ is independently hydrogen or optionally substituted alkyl; each $R_C$ is independently hydrogen or optionally substituted alkyl, heteroalkyl, aryl, heterocycle, alkylaryl, or alkylheterocycle; m is 0-4; p is 0-3; and q is 0-2.

Particular compounds of formula II are of the formula:

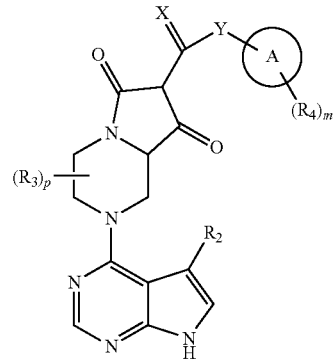

With regard to the various formulae disclosed herein, as applicable, particular embodiments of the invention are such that X is O. In others, X is $NR_A$ and $R_A$ is, for example, cyano.

In some, Y is $NR_B$ and $R_B$ is, for example, hydrogen.

In some, A is optionally substituted aryl (e.g., substituted phenyl). In others, A is optionally substituted heterocycle.

In some, $R_1$ is hydrogen.

In some, $R_2$ is optionally substituted lower alkyl (e.g., methyl).

In some, $R_3$ is optionally substituted lower alkyl (e.g., methyl).

In some, $R_4$ is halogen (e.g., bromine, fluorine). In others, $R_4$ is $R_C$, $C(O)NHR_C$, $CSO_2R_C$, or $CSO_2NHR_C$ and $R_C$ is, for example, optionally substituted lower alkyl or heteroalkyl. In particular embodiments, $R_C$ is —$(CH_2)_2N(CH_3)_2$. In some embodiments, $R_C$ is optionally substituted heterocycle (e.g., optionally substituted piperidine).

Particular compounds of the invention are potent LIMK2 inhibitors. Certain compounds have a LIMK2 $IC_{50}$ of less than about 100, 75, 50, 25 or 10 nM.

5.3. Methods of Synthesis

Compounds of the invention may be prepared by methods known in the art. See, e.g., U.S. patent publication nos. 2004/0058922 and 2005/0130954.

Pyrrolopyrimidines may be prepared by a variety of methods known in the art. See, e.g., West, *J. Org. Chem.* 26:4959 (1961); Aono et al., EP 0733633-B1. One approach is described in U.S. patent application No. 60/853,891, filed Oct. 23, 2006, and shown below in Scheme 1:

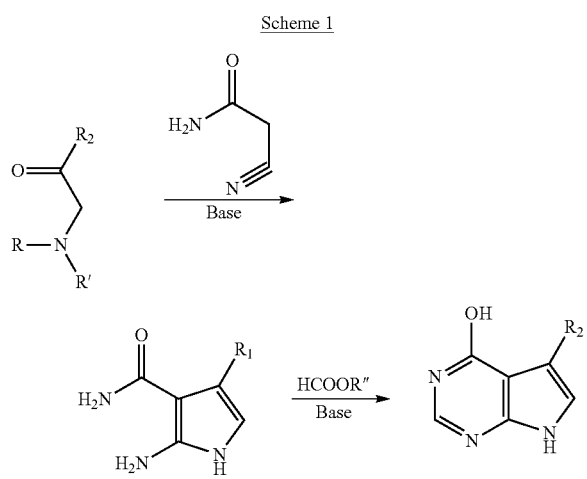

The resulting 4-hydroxy pyrrolo[2,3-d]pyrimidine compound is then converted to the corresponding 4-chloro compound (compound 1(a) in Scheme 2, below) using methods known in the art. See, e.g., West, *J. Org. Chem.* 26:4959 (1961). That compound is then used to prepare compounds of the invention, as shown below in Scheme 2:

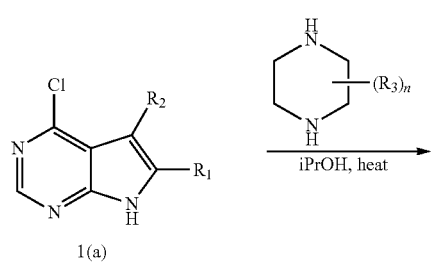

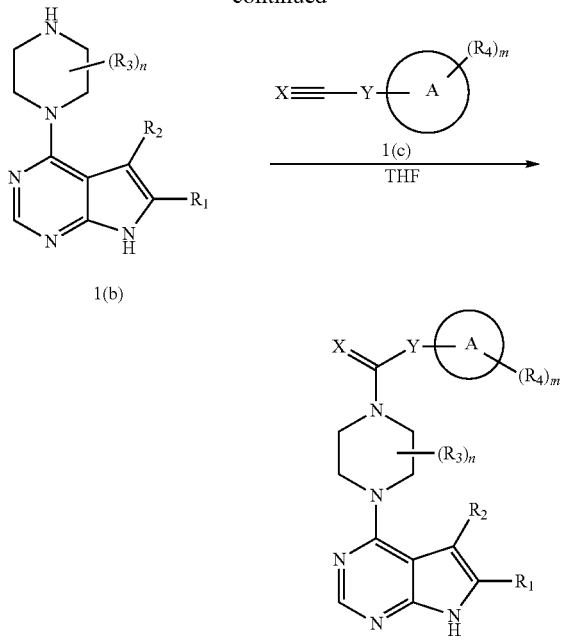

As shown in Scheme 2, the pyrrolopyrimidine 1(a) is condensed with a piperazine under suitable conditions (e.g., heating in i-PrOH) to form the substituted pyrrolopyrimidine 1(b). Treatment of this new piperazine with a suitable substituted coupling agent (e.g., an isocyanate) 1(c) produces the final compound. If desired, known can be used to transform that compound into various others encompassed by this invention.

5.4. Methods of Use

This invention encompasses a method of inhibiting LIMK2, which comprises contacting LIMK2 with a potent LIMK2 inhibitor. Preferred potent LIMK2 inhibitors are compounds of the invention (i.e., compounds disclosed herein).

A particular embodiment encompasses a method of treating, managing or preventing an inflammatory disease or disorder in a patient, which comprises administering to the patient in need thereof a therapeutically or prophylactically effective amount of a compound of the invention.

Another embodiment encompasses a method of treating, managing or preventing cancer in a patient, which comprises administering to the patient in need thereof a therapeutically or prophylactically effective amount of a compound of the invention.

Another embodiment encompasses a method of lowering intraocular pressure in a patient, which comprises inhibiting LIMK2 activity or expression in a patient in need thereof. In one method, LIMK2 activity is inhibited by contacting the eye of the patient with a potent LIMK2 inhibitor. Particular potent LIMK2 inhibitors are of formulae I or II. In another method, LIMK2 expression is inhibited by administering to the eye of the patient a compound (e.g., an siRNA) that inhibits the expression of LIMK2.

Another embodiment encompasses a method of treating, managing or preventing a diseases or disorder affecting vision in a patient, which comprises inhibiting LIMK2 activity or expression in a patient in need thereof. In one method, LIMK2 activity is inhibited by contacting the eye of the patient with a potent LIMK2 inhibitor. Particular potent LIMK2 inhibitors are of formulae I or II. In another method, LIMK2 expression is inhibited by administering to the eye of the patient a compound (e.g., an siRNA) that inhibits the expression of LIMK2. Diseases and disorders affecting vision include glaucoma, neurodegenerative diseases, and infectious diseases.

5.5. Pharmaceutical Formulations

This invention encompasses pharmaceutical compositions comprising one or more compounds of the invention. Certain pharmaceutical compositions are single unit dosage forms suitable for oral, mucosal (e.g., nasal, sublingual, vaginal, buccal, or rectal), parenteral (e.g., subcutaneous, intravenous, bolus injection, intramuscular, or intraarterial), transdermal, topical and ophthalmic (e.g., topical, intravitreal) administration to a patient.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration requires enteric coatings to protect the compounds of this invention from degradation within the gastrointestinal tract. Similarly, a formulation may contain ingredients that facilitate delivery of the active ingredient(s) to the site of action. For example, compounds may be administered in liposomal formulations, in order to protect them from degradative enzymes, facilitate transport in circulatory system, and effect delivery across cell membranes to intracellular sites.

The composition, shape, and type of a dosage form will vary depending on its use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences*, 18$^{th}$ ed. (Mack Publishing, Easton Pa.: 1990).

5.5.1. Oral Dosage Forms

Pharmaceutical compositions of the invention suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See, e.g., *Remington's Pharmaceutical Sciences*, 18$^{th}$ ed. (Mack Publishing, Easton Pa.: 1990).

Typical oral dosage forms are prepared by combining the active ingredient(s) in an intimate admixture with at least one excipient according to conventional pharmaceutical compounding techniques. Excipients can take a wide variety of forms depending on the form of preparation desired for administration.

Because of their ease of administration, tablets and capsules represent the most advantageous oral dosage unit forms. If desired, tablets can be coated by standard aqueous or non-aqueous techniques. Such dosage forms can be prepared by conventional methods of pharmacy. In general, pharmaceutical compositions and dosage forms are prepared by uniformly and intimately admixing the active ingredients with liquid carriers, finely divided solid carriers, or both, and then shaping the product into the desired presentation if necessary. Disintegrants may be incorporated in solid dosage forms to facility rapid dissolution. Lubricants may also be incorporated to facilitate the manufacture of dosage forms (e.g., tablets).

5.5.2. Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are specifically sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

5.5.3. Transdermal, Topical and Mucosal Dosage Forms

Transdermal, topical, and mucosal dosage forms include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences*, 18$^{th}$ ed. (Mack Publishing, Easton Pa.: 1990); and *Introduction to Pharmaceutical Dosage Forms*, 4$^{th}$ ed. (Lea & Febiger, Philadelphia: 1985). Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms are well known to those skilled in the pharmaceutical arts, and depend on the particular tissue to which a given pharmaceutical composition or dosage form will be applied.

Depending on the specific tissue to be treated, additional components may be used prior to, in conjunction with, or subsequent to treatment with active ingredients of the invention. For example, penetration enhancers may be used to assist in delivering active ingredients to the tissue.

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates may also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

5.5.4. Ophthalmic Dosage Forms

Compounds of the invention can be delivered to the eye using aqueous solutions, aqueous suspensions, and ointments. As those skilled in the art are aware, the ophthalmic product must be sterile in its final container to prevent microbial contamination of the eye. Preservatives may be used to maintain sterility once the container has been opened. Ophthalmic formulations also require that the pH, buffer capacity, viscosity, and tonicity of the formulation be controlled. Preferred formulations have a pH of from about 6.5 to 8.5, and a buffer capacity of from about 0.01 to 0.1. Particular formations are isotonic. Particular formations have a viscosity of from about 25 to 50 cps.

Ingredients that may be used to provide safe vehicles that effectively deliver an active pharmaceutical ingredient (API) to its site of action are well known, but will vary depending on the physical and chemical characteristics of the API.

Appropriately buffered aqueous solutions may be used for the delivery of water soluble compounds. In solution compositions, polymeric ingredients are typically used to increase the composition's viscosity. Examples of suitable polymers include cellulosic polymers (e.g., hydroxypropyl methylcellulose, hydroxyethyl cellulose, ethylhydroxyethyl cellulose), synthetic polymers (e.g., carboxyvinyl polymers, polyvinyl alcohol), polysaccharides (e.g., xanthan gum, guar gum, and dextran), and mixtures thereof. See, e.g., U.S. Pat. Nos. 4,136,173 and 7,244,440. Suspensions may also be used to deliver compounds. Polymeric ingredients are typically used in suspension compositions as physical stability aids, helping to keep the insoluble ingredients suspended or easily redispersible. Id.

Preservatives may be used to ensure the sterility of formations. Suitable preservatives include benzalkonium chloride, benzethonium chloride, chlorobutanol, phenylmercuric acetate, phenylmercuric nitrate, thimerosal, methylparaben, and propyl-parabens. And antioxidants may be used to ensure the stability of formations susceptible to oxidation. Suitable antioxidants include ethylenediaminetetraacetic acid, sodium bisulfite, sodium metabisulfite, and thiourea.

6. EXAMPLES

Aspects of this invention can be understood from the following examples, which do not limit its scope.

6.1. Example 1
(S)—N-(3-bromo-4-fluorophenyl)-2-methyl-4-(5-methyl-7H-pyrrolo[2,3-d]pyrimidin-4-yl)piperazine-1-carboxamide

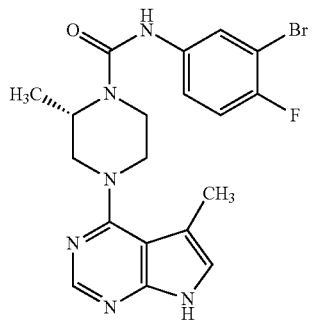 [SMILES: Cc1c[nH]c2ncnc(N3CCN(C(=O)Nc4ccc(F)c(Br)c4)[C@@H](C)C3)c12]

The captioned compound was prepared in several steps.

A. Preparation of (S)-tert-butyl 2-methyl-4-(5-methyl-7H-pyrrolo[2,3-d]pyrimidin-4-yl)piperazine-1-carboxylate (S)-tert-butyl 2-methylpiperazine-1-carboxylate (3 g, 15 mmol), N,N-diisopropylethylamine (3 ml), and 4-chloro-5-methyl-7H-pyrrolo[2,3-d]pyrimidine (2 g, 12 mmol) were added to isopropanol (10 ml). The solution was heated at 120° C. in a sealed pressure tube for 12 hours. The reaction was concentrated under vacuum, and the residue was purified by flash chromatography (80 g $SiO_2$, 0-5% MeOH: $CH_2Cl_2$, 50 min) to give clean (S)-tert-butyl 2-methyl-4-(5-methyl-7H-pyrrolo[2,3-d]pyrimidin-4-yl)piperazine-1-carboxylate (1.5 g, 4.5 mmol, 38%).

$^1$H NMR (400 MHz, chloroform-d) δ ppm 10.42 (br. s., 1H), 8.39 (s, 1H), 6.96 (s, 1H), 4.40 (d, J=6.06 Hz, 1H), 3.83-4.01 (m, 2H), 3.43 (td, J=12.57, 3.41 Hz, 1H), 3.32 (dd, J=12.76, 3.92 Hz, 1H), 3.07 (td, J=12.32, 3.41 Hz, 1H), 2.44 (s, 3H), 1.50 (s, 9H), 1.24 (d, J=6.82 Hz, 3H); MS (ES+) [M+H]$^+$=332.

B. Preparation of (S)-5-methyl-4-(3-methylpiperazin-1-yl)-7H-pyrrolo[2,3-d]pyrimidine The Boc-protected piperazine from step A (1.5 g, 4.5 mmol) was added to a 1:1 mixture of trifluoroacetic acid and dichloromethane (10 ml). The reaction was stirred overnight, then concentrated under vacuum, diluted with dichloromethane, and neutralized with sat. aq. sodium bicarbonate. The layers were separated, and the aqueous layer was back extracted with more dichloromethane. The combined organic fractions were dried over $MgSO_4$ and concentrated under vacuum to give (S)-5-methyl-4-(3-methylpiperazin-1-yl)-7H-pyrrolo[2,3-d]pyrimidine (0.80 g, 3.5 mmol, 76%).

$^1$H NMR (400 MHz, MeOD) δ ppm 8.24 (s, 1H), 7.05 (d, J=1.01 Hz, 1H), 3.97-4.04 (m, 2H), 3.00-3.14 (m, 4H), 2.74 (dd, J=12.88, 10.36 Hz, 1H), 2.45 (d, J=1.01 Hz, 3H), 1.19 (d, J=6.32 Hz, 3H); MS (ES+) [M+H]$^+$=232.

C. Preparation of (S)—N-(3-bromo-4-fluorophenyl)-2-methyl-4-(5-methyl-7H-pyrrolo[2,3-d]pyrimidin-4-yl)piperazine-1-carboxamide To a solution of triphosgene (0.30 g, 1 mmol) in $CH_2Cl_2$ (70 ml) at −5° C. were added 3-bromo-4-fluoroaniline (0.19 g, 1 mmol) in $CH_2Cl_2$ (20 ml) and triethylamine (0.60 ml, 4.3 mmol). The reaction was stirred at room temperature for 20 min, then (S)-5-methyl-4-(3-methylpiperazin-1-yl)-7H-pyrrolo[2,3-d]pyrimidine from step B (0.23 g, 1 mmol) in $CH_2Cl_2$ (30 ml) was added. The mixture was stirred for 1.5 hours, then concentrated under vacuum. The residue was purified by prep HPLC to afford (S)—N-(3-bromo-4-fluorophenyl)-2-methyl-4-(5-methyl-7H-pyrrolo[2,3-d]pyrimidin-4-yl)piperazine-1-carboxamide (65 mg) as a white solid.

$^1$H NMR (400 MHz, methanol-$d_4$) δ ppm 8.36 (s, 1H), 7.74 (dd, J=6.3, 2.5 Hz, 1H), 7.35 (ddd, J=8.9, 4.2, 2.6 Hz, 1H), 7.24 (d, J=1.0 Hz, 1H), 7.13 (t, J=8.7 Hz, 1H), 4.55-4.62 (m, 1H), 4.33-4.41 (m, 1H), 4.18 (dd, J=13.0, 1.3 Hz, 1H), 4.04-4.12 (m, 1H), 3.85 (dd, J=13.0, 4.0 Hz, 1H), 3.57-3.68 (m, 2H), 2.49 (d, J=1.0 Hz, 3H), 1.28 (d, J=6.8 Hz, 3H); MS (ES+) [M+H]$^+$=447.3.

6.2. Example 2

(S)-3-(2-methyl-4-(5-methyl-7H-pyrrolo[2,3-d]pyrimidin-4-yl)piperazine-1-carboxamido)phenyl dimethylcarbamate

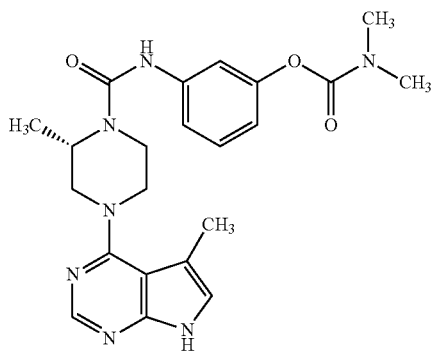

A. Preparation of 3-aminophenyl-N,N-dimethylcarbamate 3-nitrophenol (1.0 g, 7.2 mmol) was treated with pyridine (1.7 ml, 21.6 mmol), triethylamine (1.5 ml, 10.8 mmol), and N,N-dimethylchlorocarbamate (0.79 ml, 8.6 mmol) for 3 days. The reaction was quenched with $H_2O$, stirred for 15 min, diluted with $Et_2O$, washed with 1 M aq. $NaHSO_4$, $H_2O$, sat. aq. $NaHCO_3$, and brine (with back extraction), dried over $MgSO_4$, filtered, and concentrated under vacuum. The residue was hydrogenated with balloon pressure $H_2$ over 10% Pd/C (50% wet, 1.26 g, 0.59 mmol) in THF (36 ml) with AcOH (0.42 ml) for 18 hours. The reaction was filtered through celite with EtOAc and concentrated under vacuum. The residue was purified by flash chromatography (40 g $SiO_2$, 0-4% $MeOH:CH_2Cl_2$) to give 3-aminophenyl-N,N-dimethylcarbamate (1.15 g, 6.4 mmol, 89%).

$^1H$ NMR (400 MHz, chloroform-d) δ ppm 7.12 (t, J=8.0 Hz, 1H), 6.52 (t, J=2.3 Hz, 1H), 6.50 (t, J=2.3 Hz, 1H), 6.46 (t, J=2.1 Hz, 1H), 3.71 (br. s., 2H), 3.08 (s, 3H), 3.01 (s, 3H); MS (ES+) $[M+H]^+=181$.

B. Preparation of (S)-3-(2-methyl-4-(5-methyl-7H-pyrrolo[2,3-d]pyrimidin-4-yl)piperazine-1-carboxamido)phenyl dimethylcarbamate To a solution of triphosgene (104 mg, 0.35 mmol) in anhydrous THF (7.5 ml) at 0° C. was added slowly 3-aminophenyl-N,N-dimethylcarbamate from step A (180 mg, 1.0 mmol) in THF (2.5 ml). The reaction was stirred for 15 min. at 0° C. and 15 min. at room temperature. (S)-5-methyl-4-(3-methylpiperazin-1-yl)-7H-pyrrolo[2,3-d]pyrimidine from Example 1, step B (231 mg, 1.0 mmol) was added. The reaction was stirred 1 hour, quenched with MeOH, diluted with EtOAc, washed with $H_2O$, sat. aq. $NaHCO_3$ and brine, dried over $MgSO_4$, filtered, and concentrated under vacuum. The residue was purified by flash chromatography (40 g $SiO_2$, 0-8% $MeOH:CH_2Cl_2$) and lyophilized to give (S)-3-(2-methyl-4-(5-methyl-7H-pyrrolo[2,3-d]pyrimidin-4-yl)piperazine-1-carboxamido)phenyl dimethylcarbamate (365 mg, 0.84 mmol, 84%) as a white solid.

$^1H$ NMR (400 MHz, chloroform-d) δ ppm 9.82 (br. s., 1H), 8.40 (s, 1H), 7.31 (t, J=2.1 Hz, 1H), 7.24 (t, J=8.2 Hz, 1H), 7.10-7.19 (m, 1H), 6.95 (s, 1H), 6.80 (dd, J=6.8, 1.3 Hz, 1H), 6.60 (s, 1H), 4.37 (ddd, J=6.2, 3.3, 3.2 Hz, 1H), 4.14 (dd, J=12.5, 1.4 Hz, 1H), 3.91-3.98 (m, 2H), 3.54 (td, J=12.3, 3.3 Hz, 1H), 3.45 (dd, J=12.9, 4.0 Hz, 1H), 3.18 (td, J=12.3, 3.5 Hz, 1H), 3.09 (s, 3H), 3.01 (s, 3H), 2.45 (d, J=1.0 Hz, 3H), 1.32 (d, J=6.6 Hz, 3H); MS (ES+) $[M+H]^+=438$.

6.3. Example 3

N-(3-bromophenyl)-3-(5-methyl-7H-pyrrolo[2,3-d]pyrimidin-4-yl)-3,8-diazabicyclo[3.2.1]octane-8-carboxamide

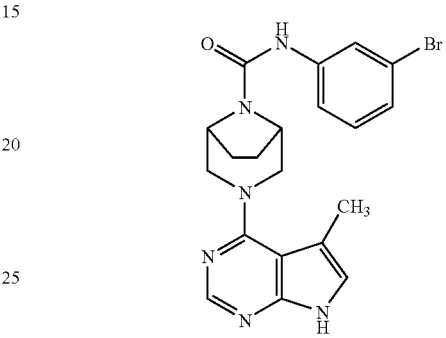

A. Preparation of tert-butyl 3-(5-methyl-7H-pyrrolo[2,3-d]pyrimidin-4-yl)-3,8-diazabicyclo[3.2.1]octane-8-carboxylate To a solution of 4-chloro-5-methyl-7H-pyrrolo[2,3-d]pyrimidine (25 mg, 0.15 mmol) and tert-butyl 3,8-diazabicyclo[3.2.1]octane-8-carboxylate (30 mg, 0.14 mmol) in isopropanol (2 ml) was added triethylamine (36 µL, 0.26 mmol). The reaction was heated at 180° C. for 30 min in the microwave, then concentrated under vacuum. The residue was purified by prep HPLC (Sunfire C18 30×50 mm, 10-90% $H_2O$/MeOH w/0.01% TFA, 15 min, 35 ml/min, 220 nm) to give tert-butyl 3-(5-methyl-7H-pyrrolo[2,3-d]pyrimidin-4-yl)-3,8-diazabicyclo[3.2.1]octane-8-carboxylate (35 mg, 0.10 mmol, 66%).

B. Preparation of 4-(3,8-diazabicyclo[3.2.1]octan-3-yl)-5-methyl-7H-pyrrolo[2,3-d]pyrimidine dihydrochloride Boc-protected diazabicyclo[3.2.1]octane from step A was dissolved in 4M HCl in dioxane (4 ml). The reaction was stirred for 1 hour and concentrated under vacuum to afford 4-(3,8-diazabicyclo[3.2.1]octan-3-yl)-5-methyl-7H-pyrrolo[2,3-d]pyrimidine dihydrochloride (30 mg, 0.093 mmol, 91%).

C. Preparation of N-(3-bromophenyl)-3-(5-methyl-7H-pyrrolo[2,3-d]pyrimidin-4-yl-3,8-diazabicyclo[3.2.1]octane-8-carboxamide The diazabicyclo[3.2.1]octane from step B was dissolved in dry THF (3 ml) under $N_2$, and 3-bromoisocyanate (30 µL, 0.11 mmol) was added. After stirring for 3 hours, the reaction was concentrated, and the residue was purified by prep HPLC to give 1.5 mg of N-(3-bromophenyl)-3-(5-methyl-7H-pyrrolo[2,3-d]pyrimidin-4-yl)-3,8-diazabicyclo[3.2.1]octane-8-carboxamide.

¹H NMR (MeOD): δ 5.45 (1H, s), 7.69 (1H, s), 7.3 (1H, m), 7.1 (3H, m), 4.52 (2H, m), 2.2 (2H, J=12.4 Hz, d), 2.18 (2H, J=12.4 Hz, d), 2.38 (3H, s), 1.94 (2H, m), 2.25 (2H, m); MS (ES+) [M+H]⁺=443.

6.4. Example 4

2-(3-bromophenyl)-7-(5-methyl-7H-pyrrolo[2,3-d]pyrimidin-4-yl)tetrahydroimidazo[1,5-a]pyrazine-1,3 (2H,5H)-dione

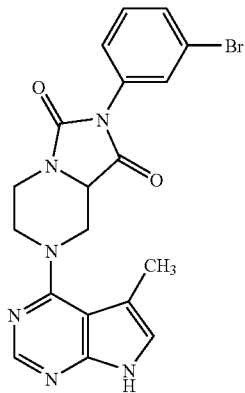 [SMILES: Cc1c[nH]c2ncnc(N3CCN4C(=O)N(c5cccc(Br)c5)C(=O)C4C3)c12]

To a solution of methyl 4-(5-methyl-7H-pyrrolo[2,3-d]pyrimidin-4-yl)piperazine-2-carboxylate prepared analogously to the piperazine from Example 1, step B (30 mg, 0.1 mmol) in 1.5 ml of CH₂Cl₂ was added slowly 3-bromoisocyanate (13 μL, 0.1 mmol). The mixture was stirred at room temperature until the starting material was consumed (monitoring by LC/MS). The solvent was removed under vacuum, and the residue was purified by Prep-HPLC to give 2-(3-bromophenyl)-7-(5-methyl-7H-pyrrolo[2,3-d]pyrimidin-4-yl)tetrahydroimidazo[1,5-a]pyrazine-1,3(2H,5H)-dione as a white solid.

¹H NMR (CD₃OD): δ 8.27 (s, 1H), 7.71 (s, 1H), 7.39-7.58 (m, 3H), 7.16 (s, 1H), 4.58-4.62 (m, 1H), 4.49-4.51 (m, 1H), 4.15-4.21 (m, 2H), 3.20-3.41 (m, 3H), 2.46 (s, 3H); MS (ES+) [M+H]⁺=441, 443.

6.5. Example 5

(S)—N-(3-bromophenyl)-N'-cyano-2-methyl-4-(5-methyl-7H-pyrrolo[2,3-d]pyrimidin-4-yl)piperazine-1-carboximidamide

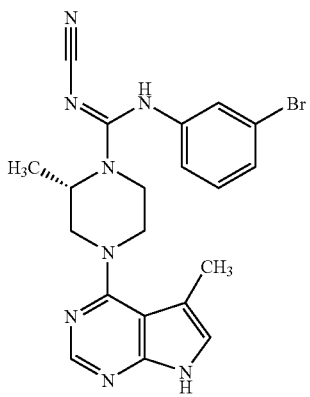 [SMILES: Cc1c[nH]c2ncnc(N3CCN(/C(=N/C#N)Nc4cccc(Br)c4)[C@@H](C)C3)c12]

A. Preparation of phenyl N-3-bromophenyl-N'-cyanocarbamimidate 3-bromoaniline (1.44 g, 8.4 mmol), diphenyl-N-cyanocarbonimidate (2 g, 8.4 mmol) were added to acetonitrile (20 ml). The solution was heated at 50° C. overnight and cooled to room temperature, resulting in precipitation of the product. The white crystalline solid was filtered to give phenyl N-3-bromophenyl-N'-cyanocarbamimidate (2 g, 6.3 mmol, 75%).

¹H NMR (400 MHz, CHLOROFORM-d) δ ppm 7.59 (t, J=2.02 Hz, 1H), 7.42-7.47 (m, 2H), 7.40 (ddd, J=8.15, 1.45, 1.26 Hz, 1H), 7.31-7.36 (m, 2H), 7.24-7.29 (m, 2H), 7.13-7.18 (m, 1H); MS (ES+) [M+H]⁺=316, 318.

B. Preparation of (S)—N-(3-bromophenyl)-N'-cyano-2-methyl-4-(5-methyl-7H-pyrrolo[2,3-d]pyrimidin-4-yl)piperazine-1-carboximidamide The cyanocarbamimidate from step A (9.48 g, 30 mmol), (S)-5-methyl-4-(3-methylpiperazin-1-yl)-7H-pyrrolo[2,3-d]pyrimidine from Example 1, step B (6.93 g, 30 mmol), and triethylamine (4.16 ml, 30 mmol) were combined in MeCN (250 ml) and heated to 85° C. for 6 hours. The reaction was cooled to room temperature and concentrated under vacuum. The residue was purified by flash chromatography (750 g SiO₂, 0-7% MeOH:CH₂Cl₂) to give a yellow foam. This material was dissolved in MeOH and stirred with activated charcoal at 60° C. for 15 min. The mixture was filtered through celite, washing with copious amounts of MeOH and 10% MeOH:CH₂Cl₂, and concentrated under vacuum. The residue was purified again by flash chromatography (750 g SiO₂, 0-7% MeOH:CH₂Cl₂). The resulting material was dissolved in MeOH, and water was added to crash out the product. The mixture was concentrated under vacuum, and the product was resuspended in water and lyophilized to give a hydrate of (S)—N-(3-bromophenyl)-N'-cyano-2-methyl-4-(5-methyl-7H-pyrrolo[2,3-d]pyrimidin-4-yl)piperazine-1-carboximidamide (8.17 g, 57%, 1.25 eq. H₂O based on CHN analysis) as an amorphous white solid.

¹H NMR (400 MHz, DMSO) δ ppm 11.60 (s, 1H), 9.50 (s, 1H), 8.22 (s, 1H), 7.25 (m, 3H), 7.07 (m, 2H), 4.51 (m, 1H), 4.00 (m, 1H), 3.91 (m, 1H), 3.84 (m, 1H), 3.53 (m, 1H), 3.32 (m, 1H), 3.08 (m, 1H), 2.37 (d, J=1.0 Hz, 3H), 1.24 (d, J=6.6 Hz, 3H); MS (ES+) [M+H]⁺=453, 455; CHN Anal. Calcd for C₂₀H₂₁BrN₈·1.25H₂O: C, 50.48; H, 4.98; N, 23.55. Found: C, 50.18; H, 4.58; N, 23.53.

6.6. Example 6

(S)—N-(3-chlorophenyl)-N'-cyano-2-methyl-4-(5-methyl-7H-pyrrolo[2,3-d]pyrimidin-4-yl)piperazine-1-carboximidamide

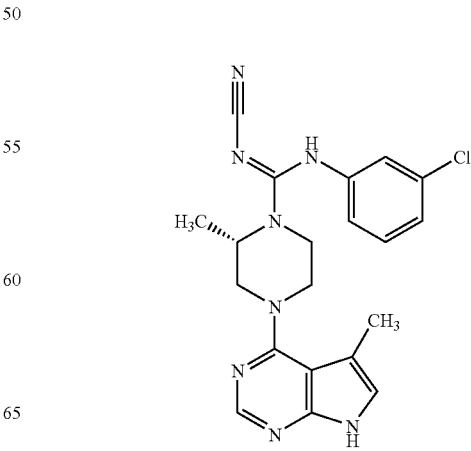

A. Preparation of phenyl N-3-chlorophenyl-N'-cyanocarbamimidate

Diphenyl-N-cyanocarbonimidate (2 g, 8.4 mmol) and 3-chloroaniline (0.88 ml, 8.4 mmol) were added to acetonitrile (20 ml). The solution was heated at 50° C. overnight and cooled to room temperature, resulting in precipitation of the product. The white crystalline solid was filtered to give phenyl N-3-chlorophenyl-N'-cyanocarbamimidate (2 g, 7.3 mmol, 88%).

$^1$H NMR (400 MHz, chloroform-d) δ ppm 7.42-7.48 (m, 3H), 7.28-7.36 (m, 2H), 7.24-7.27 (m, 2H), 7.13-7.18 (m, 2H); MS (ES+) [M+H]$^+$=272.

B. Preparation of (S)—N-(3-chlorophenyl)-N'-cyano-2-methyl-4-(5-methyl-7H-pyrrolo[2,3-d]pyrimidin-4-yl)piperazine-1-carboximidamide The cyanocarbamimidate from step A (0.47 g, 1.7 mmol), (S)-5-methyl-4-(3-methylpiperazin-1-yl)-7H-pyrrolo[2,3-d]pyrimidine from Example 1, step B (0.40 g, 1.7 mmol), and N,N-diisopropylethylamine (1 ml) were added to acetonitrile (10 ml). The mixture was heated at 85° C. in a sealed pressure tube for 4 hours. The solvent was evaporated, and the residue was purified by flash chromatography (80 g SiO$_2$, 0-5% MeOH:CH$_2$Cl$_2$, 50 min) to give (S)—N-(3-chlorophenyl)-N'-cyano-2-methyl-4-(5-methyl-7H-pyrrolo[2,3-d]pyrimidin-4-yl)piperazine-1-carboximidamide (0.32 g, 0.79 mmol, 46%).

$^1$H NMR (400 MHz, MeOD) δ ppm 8.22 (s, 1H), 7.31 (t, J=7.96 Hz, 1H), 7.01-7.16 (m, 4H), 4.15 (d, J=13.14 Hz, 1H), 4.00 (d, J=13.39 Hz, 1H), 3.91 (d, J=13.14 Hz, 1H), 3.65 (d, J=3.28 Hz, 1H), 3.47 (dd, J=13.14, 3.79 Hz, 1H), 3.34 (s, 1H), 3.09-3.25 (m, 1H), 2.44 (s, 3H), 1.32 (d, J=6.57 Hz, 3H); MS (ES+) [M+H]$^+$=409.

6.7. Example 7

(S)—N'-cyano-N-(3-fluorophenyl)-2-methyl-4-(5-methyl-7H-pyrrolo[2,3-d]pyrimidin-4-yl)piperazine-1-carboximidamide

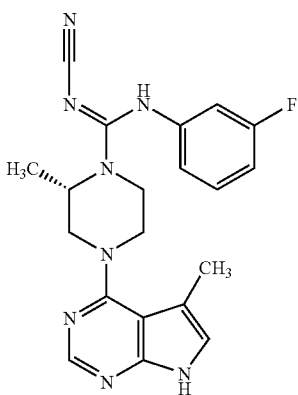 [SMILES: Cc1c[nH]c2ncnc(N3CCN(/C(=N/C#N)Nc4cccc(F)c4)[C@@H](C)C3)c12]

Phenyl N'-cyano-N-(3-fluorophenyl)carbamimidate, prepared analogously to phenyl N-3-chlorophenyl-N'-cyanocarbamimidate from Example 6, step A, (0.55 g, 2.2 mmol), (S)-5-methyl-4-(3-methylpiperazin-1-yl)-7H-pyrrolo[2,3-d]pyrimidine, from example 1, step B, (0.50 g, 2.2 mmol), and N,N-diisopropylethylamine (1 ml) were added to acetonitrile (10 ml). The mixture was heated at 85° C. in a sealed pressure tube for 4 hours. The solvent was evaporated, and the residue was purified prep HPLC (Sunfire C18 30×250 mm column. 10-100% MeCN:H$_2$O (10 mM NH4OAc), 18 min., 45 ml/min) to give (S)—N'-cyano-N-(3-fluorophenyl)-2-methyl-4-(5-methyl-7H-pyrrolo[2,3-d]pyrimidin-4-yl)piperazine-1-carboximidamide (0.23 g, 0.58 mmol, 27%).

$^1$H NMR (400 MHz, MeOD) δ ppm 8.28 (s, 1H), 7.31-7.49 (m, 1H), 7.08 (d, J=1.01 Hz, 1H), 6.89-7.02 (m, 2H), 4.63-4.74 (m, 1H), 4.20 (d, J=13.14 Hz, 1H), 4.06 (d, J=13.39 Hz, 1H), 3.97 (d, J=11.12 Hz, 1H), 3.67-3.86 (m, 1H), 3.54 (dd, J=13.14, 3.79 Hz, 1H), 3.38 (br. s., 2H), 3.18-3.29 (m, 1H), 2.50 (d, J=1.01 Hz, 2H), 1.39 (d, J=6.57 Hz, 3H); MS (ES+) [M+H]$^+$=393.

6.8. Example 8

(S)—N'-cyano-2-methyl-4-(5-methyl-7H-pyrrolo[2,3-d]pyrimidin-4-yl)-N-(3-(trifluoromethyl)phenyl)piperazine-1-carboximidamide

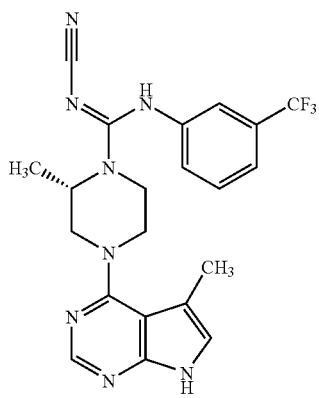 [SMILES: Cc1c[nH]c2ncnc(N3CCN(/C(=N/C#N)Nc4cccc(C(F)(F)F)c4)[C@@H](C)C3)c12]

Phenyl N'-cyano-N-(3-(trifluoromethyl)phenyl)carbamimidate, prepared analogously to N-3-bromophenyl-N'-cyanocarbamimidate from Example 5, step A (36 mg, 0.12 mmol), (S)-5-methyl-4-(3-methylpiperazin-1-yl)-7H-pyrrolo[2,3-d]pyrimidine, from Example 1, step B, (35 mg, 0.15 mmol), and triethylamine (0.05 ml, 0.36 mmol) were combined in isopropanol in a microwave vessel. The reaction was heated at 140° C. for 30 min. under microwave conditions. The solvent was evaporated, and the residue was washed with CH$_2$Cl$_2$ (3×10 ml). The crude product was purified by Prep-HPLC to afford (S)—N'-cyano-2-methyl-4-(5-methyl-7H-pyrrolo[2,3-d]pyrimidin-4-yl)-N-(3-(trifluoromethyl)phenyl)-piperazine-1-carboximidamide as white solid.

$^1$H(CD$_3$OD): δ1.349-1.65 (3H, J=6.4 Hz, d), 2.028-2.054 (broad, N—H); 3.515-3.547 (1H, m), 3.611-3.736 (2H, m), 4.059-4.092 (1H, J=13.2 Hz, d), 4.561-4.595 (1H, J=13.6 Hz, d), 4.643-4.706 (2H, m) 6.70 (1H, s), 7.19 (1H, s), 7.428-7.449 (2H, m), 7.549-7.588 (2H, m), 8.203 (1H, s, broad); MS (ES+) [M+H]$^+$=429.

6.9. Example 9

(S)—N-(3-bromo-4-fluorophenyl)-N'-cyano-2-methyl-4-(5-methyl-7H-pyrrolo[2,3-d]pyrimidin-4-yl)piperazine-1-carboximidamide

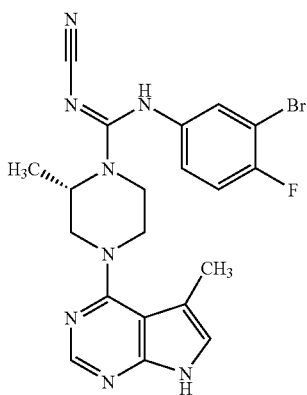 [SMILES: Cc1c[nH]c2ncnc(N3CCN(/C(=N/C#N)Nc4ccc(F)c(Br)c4)[C@@H](C)C3)c12]

The title compound was prepared in the same manner as (S)—N-(3-chlorophenyl)-N'-cyano-2-methyl-4-(5-methyl-7H-pyrrolo[2,3-d]pyrimidin-4-yl)piperazine-1-carboximidamide from Example 6.

$^1$H NMR (400 MHz, MeOD) δ ppm 8.23 (s, 1H), 7.42 (dd, J=5.8, 2.5 Hz, 1H), 7.13-7.24 (m, 2H), 7.04 (s, 1H), 4.62 (br. s., 1H), 4.16 (d, J=13.1 Hz, 1H), 4.03 (d, J=13.4 Hz, 1H), 3.92 (d, J=13.1 Hz, 1H), 3.63-3.73 (m, 1H), 3.49 (dd, J=13.0, 3.7 Hz, 1H), 3.21 (td, J=12.4, 3.3 Hz, 1H), 2.45 (s, 3H), 1.33 (d, J=6.6 Hz, 3H); MS (ES+) [M+H]$^+$=471, 473.

6.10. Example 10

N-(3-bromophenyl)-N'-cyano-2,5-dimethyl-4-(5-methyl-7H-pyrrolo[2,3-d]pyrimidin-4-yl)piperazine-1-carboximidamide

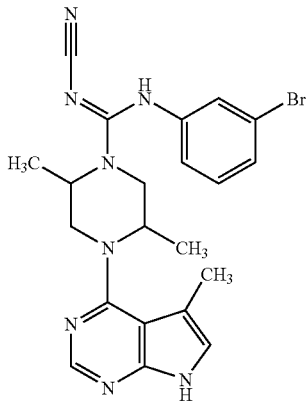 [SMILES: Cc1c[nH]c2ncnc(N3CC(C)N(/C(=N/C#N)Nc4cccc(Br)c4)CC3C)c12]

A. Preparation of 4-(2,5-dimethylpiperazin-1-yl)-5-methyl-7H-pyrrolo[2,3-d]pyrimidine Trans-2,5-dimethylpiperazine (1 g, 8.8 mmol), N,N-diisopropylethylamine (1 ml) and 4-chloro-5-methyl-7H-pyrrolo[2,3-d]pyrimidine (2 g, 11.9 mmol) were added to isopropanol (10 ml). The solution was heated in a microwave at 150° C. for 6 hours, then concentrated under vacuum. The material was purified by prep HPLC (Sunfire C18 30×250 mm column. 10-100% MeCN:H$_2$O (10 mM NH$_4$OAc), 18 min., 45 ml/min.) to give 4-(trans-2,5-dimethylpiperazin-1-yl)-5-methyl-7H-pyrrolo[2,3-d]pyrimidine (0.30 g, 14%).

$^1$H NMR (400 MHz, chloroform-d) δ ppm 8.49 (s, 1H), 6.95 (s, 1H), 3.62-3.70 (m, 1H), 3.46-3.57 (m, 1H), 3.20-3.27 (m, 1H), 2.95 (q, J=7.41 Hz, 1H), 2.81 (dd, J=12.63, 9.60 Hz, 1H), 2.08 (s, 3H), 1.31 (d, J=6.82 Hz, 3H), 1.15 (t, J=6.57 Hz, 4H); MS (ES+) [M+H]$^+$=246.

B. Preparation of N-(3-bromophenyl)-N'-cyano-2,5-dimethyl-4-(5-methyl-7H-pyrrolo[2,3-d]pyrimidin-4-yl)piperazine-1-carboximidamide The dimethyl piperazine from step A (80 mg, 0.32 mmol), phenyl N-3-bromophenyl-N'-cyanocarbamimidate, from Example 5, step A, (100 mg, 0.32 mmol) and N,N-diisopropylethylamine (0.20 ml) were added to isopropanol (10 ml). The mixture was heated at 150° C. for 20 min in a microwave, then concentrated under vacuum. The material was purified prep HPLC (Sunfire C18 30×250 mm column, 10-100% MeCN:H$_2$O (10 mM NH$_4$OAc), 18 min., 45 ml/min) to give (E)-N-(3-bromophenyl)-N'-cyano-2,5-dimethyl-4-(5-methyl-7H-pyrrolo[2,3-d]pyrimidin-4-yl)piperazine-1-carboximidamide (29 mg, 0.062 mmol, 19%).

$^1$H NMR (400 MHz, MeOD) δ ppm 8.21 (s, 1H), 7.23-7.32 (m, 3H), 7.08-7.15 (m, 1H), 7.02 (s, 1H), 4.60 (br. s., 2H), 3.85 (d, J=2.53 Hz, 3H), 3.63 (d, J=12.38 Hz, 1H), 2.43 (s, 3H), 1.26 (d, J=6.82 Hz, 3H), 1.18 (d, J=6.57 Hz, 3H); MS (ES+) [M+H]$^+$=469.

6.11. Example 11

(S)—N-(3-bromophenyl)-N'-cyano-2-isopropyl-4-(5-methyl-7H-pyrrolo[2,3-d]pyrimidin-4-yl)piperazine-1-carboximidamide

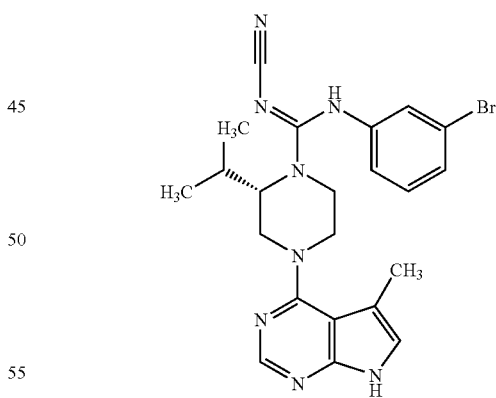

A. Preparation of (S)-4-(3-isopropylpiperazin-1-yl)-5-methyl-7H-pyrrolo[2,3-d]pyrimidine To a solution of (S)-3-isopropylpiperazine-2,5-dione (100 mg, 0.6 mmol) in anhydrous THF was added lithium aluminum hydride 1M in THF (1.2 ml, 1.2 mmol). The reaction refluxed for 1 hr, cooled to room temperature, quenched with H$_2$O, filtered, then concentrated under vacuum to yield (S)-2-isopropylpiperazine. This material was combined with 4-chloro-5-methyl-7H-pyrrolo[2,3-d]pyrimidine (85.5 mg, 0.5 mmol) in triethylamine (1 ml) and isopropanol (2 ml). The reaction was heated in a microwave at 180° C. for 30 min, concentrated under vacuum, dissolved in EtOAc, washed with H₂O, and concentrated under vacuum to afford (S)-4-(3-isopropylpiperazin-1-yl)-5-methyl-7H-pyrrolo[2,3-d]pyrimidine, carried on without further purification.

B. Preparation of (S)—N-(3-bromophenyl)-N'-cyano-2-isopropyl-4-(5-methyl-7H-pyrrolo[2,3-d]pyrimidin-4-yl)piperazine-1-carboximidamide The piperazine from step A was combined with phenyl N-3-bromophenyl-N'-cyanocarbamimidate, from example 5, step A, (40 mg, 1.2 mmol) in isopropanol in a sealed tube. The reaction was heated to 120° C., monitored by LC/MS until no starting material remained, and then concentrated under vacuum. The residue was purified by prep HPLC (Sunfire C18 5u 30×100 mm, 10% to 100% B, gradient time=13 min, flow rate=45 ml/min, wavelength=220 nm, solvent A=10 mM aq. Ammonium acetate, solvent B=acetonitrile) to give (S)—N-(3-bromophenyl)-N'-cyano-2-isopropyl-4-(5-methyl-7H-pyrrolo[2,3-d]pyrimidin-4-yl)piperazine-1-carboximidamide (2.2 mg, 7%) as a white solid.

¹H NMR (400 MHz, MeOD) δ (ppm) 8.35 (s, 1H), 7.3 (d, 1H), 7.29 (m, 1H), 7.1 (s, 1H) 7.19 (s, 1H), 7.13 (d, 1H), 3.6 dm, 2H), 3.5 (m, 2H), 3.3 (m, 2H), 2.46 (s, 3H), 1.44 (m, 2H), 0.93 (m, 6H); MS (ES+) [M+H]⁺=482.

6.12. Example 12

(S)—N-(3-bromophenyl)-N'-cyano-4-(5-methyl-7H-pyrrolo[2,3-d]pyrimidin-4-yl)-2-(2-(methylthio)ethyl)piperazine-1-carboximidamide

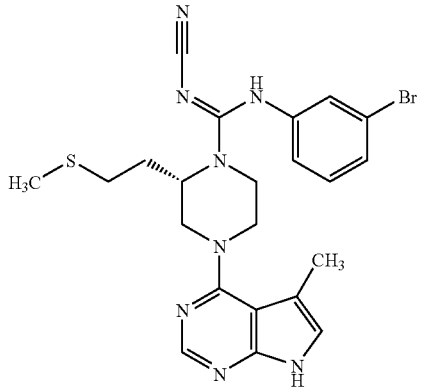 [SMILES: CSCC[C@H]1CN(c2ncnc3[nH]cc(C)c23)CCN1/C(=N/C#N)Nc1cccc(Br)c1]

A. Preparation of (S)-3-(2-(methylthio)ethyl)piperazine-2,5-dione

L-methionine methyl ester HCl (1 g, 5 mmol) was taken up in CH₂Cl₂ and chloroacetyl chloride (598 µL, 7.5 mmol) was added with stirring. After 10 minutes of stirring, aqueous saturated NaOH (1 ml) was added. The reaction was stirred for 20 minutes, and the CH₂Cl₂ layer was separated, washed with H₂O (2×), and concentrated under vacuum. The residue was treated with 7N ammonia in MeOH at 100° C. for 1.5 hr. The reaction was concentrated under vacuum to yield (S)-3-(2-(methylthio)ethyl)piperazine-2,5-dione to be used crude.

B. Preparation of (S)—N-(3-bromophenyl)-N'-cyano-4-(5-methyl-7H-pyrrolo[2,3-d]pyrimidin-4-yl)-2-(2-(methylthio)ethyl)piperazine-1-carboximidamide Using the dione from step A, the title compound was prepared in the same manner as (S)—N-(3-bromophenyl)-N'-cyano-2-isopropyl-4-(5-methyl-7H-pyrrolo[2,3-d]pyrimidin-4-yl)piperazine-1-carboximidamide from Example 11.

¹H NMR (400 MHz, MeOD) δ (ppm) 8.35 (s, 1H), 7.3 (d, 1H), 7.29 (m, 1H), 7.1 (s, 1H) 7.19 (s, 1H), 7.13 (d, 1H), 4.24 (M, 2 h), 3.99 (m, 1H), 3.6 (m, 2H), 3.4 (m, 2H), 2.4 (m, 2H), 2.3 (s, 3H), 1.97 (m, 1H), 1.91 (s, 3H), 1.79 (m, 1H); MS (ES+) [M+H]⁺=514.

6.13. Example 13

(S)-phenyl N-cyano-2-methyl-4-(5-methyl-7H-pyrrolo[2,3-d]pyrimidin-4-yl)piperazine-1-carbimidate

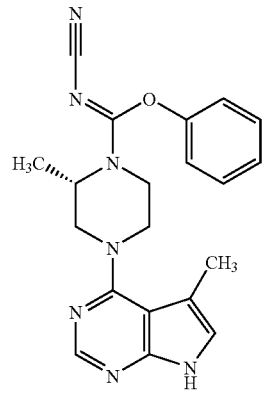 [SMILES: Cc1c[nH]c2ncnc(N3CCN(/C(=N/C#N)Oc4ccccc4)[C@@H](C)C3)c12]

(S)-5-Methyl-4-(3-methylpiperazin-1-yl)-7H-pyrrolo[2,3-d]pyrimidine, from Example 1, step B, (347 mg, 1.5 mmol) and diphenyl-N-cyanocarbonimidate (357 mg, 1.5 mmol) were combined in acetonitrile (3 ml) and heated at 50° C. for 2 hours, then stirred overnight at room temperature. The reaction was concentrated under vacuum, and the residue was purified by flash chromatography (40 g SiO₂, 0-5% MeOH:CH₂Cl₂) to give (S)-phenyl N-cyano-2-methyl-4-(5-methyl-7H-pyrrolo[2,3-d]pyrimidin-4-yl)piperazine-1-carbimidate (481 mg, 1.3 mmol, 86%) as an off-white solid.

¹H NMR (400 MHz, MeOD) δ ppm 8.24 (s, 1H), 7.41-7.47 (m, 2H), 7.28 (t, J=7.5 Hz, 1H), 7.18 (d, J=7.6 Hz, 2H), 7.04 (d, J=1.0 Hz, 1H), 4.72 (br. s., 1H), 4.17-4.29 (m, 2H), 3.96 (dt, J=13.4, 1.9 Hz, 1H), 3.78 (ddd, J=13.5, 11.9, 3.4 Hz, 1H), 3.55 (dd, J=13.4, 4.0 Hz, 1H), 3.21-3.29 (m, 1H), 2.45 (d, J=1.0 Hz, 3H), 1.38 (d, J=6.8 Hz, 3H); MS (ES+) [M+H]$^+$= 376.

6.14. Example 14

(S)—N-(3-bromophenyl)-N'-cyano-2-methyl-4-(6-methyl-7H-pyrrolo[2,3-d]pyrimidin-4-yl)piperazine-1-carboximidamide

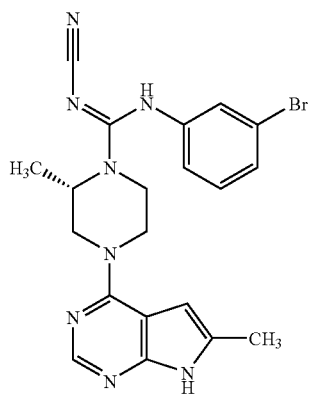 [SMILES: Cc1cc2c(N3CCN(/C(=N/C#N)Nc4cccc(Br)c4)[C@@H](C)C3)ncnc2[nH]1]

A. Preparation of 4-chloro-6-methyl-7H-pyrrolo[2,3-d]pyrimidine

In a sealed tube, ethyl 2-amino-5-methyl-1H-pyrrole-3-carboxylate (150 mg, 0.9 mmol, prepared according to literature procedures, *J. Heterocyclic Chem.*, 23:1555 (1985)) was dissolved in formamide (4.5 ml), formic acid (2.3 ml) and DMF (1.0 ml) and heated to 155° C. for 12 h. The reaction was concentrated, taken up with NaHCO$_3$ solution, and extracted with DCM to afford 6-methyl-7H-pyrrolo[2,3-d]pyrimidin-4-ol (70 mg, 0.46 mmol, 51%, MS (ES+) [M+H]$^+$=150). This material was dissolved in phosphorous oxychloride (5 ml) and heated to 110° C. for 1 h. The reaction was concentrated, taken up with NaHCO$_3$, and extracted with DCM to give 4-chloro-6-methyl-7H-pyrrolo[2,3-d]pyrimidine (40 mg, 0.23 mmol, 50%). MS (ES+) [M+H]$^+$=168.

B. Preparation of (S)—N-(3-bromophenyl)-N'-cyano-2-methyl-4-(6-methyl-7H-pyrrolo[2,3-d]pyrimidin-4-yl)piperazine-1-carboximidamide Using the pyrrolopyrimidine from step A, the title compound was prepared in the same manner as (S)—N-(3-bromophenyl)-N'-cyano-2-methyl-4-(5-methyl-7H-pyrrolo[2,3-d]pyrimidin-4-yl)piperazine-1-carboximidamide from Example 5.
$^1$H NMR (CD$_3$OD): δ 8.12 (1H, s), 7.29 (3H, m), 7.12 (1H, m), 6.38 (1H, s), 4.59 (2H, m), 4.83 (1H, J=13.6 Hz, d), 3.72 (3H, m), 2.4 (3H, s), 1.31 (3H, J=6.8 Hz, d); MS (ES+) [M+H]$^+$=455.

6.15. Example 15

(S)—N-(3-bromophenyl)-4-(5-chloro-7H-pyrrolo[2,3-d]pyrimidin-4-yl)-N'-cyano-2-methylpiperazine-1-carboximidamide

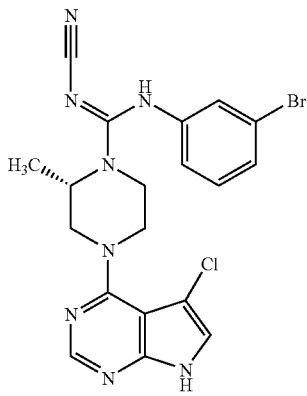 [SMILES: C[C@H]1CN(c2ncnc3[nH]cc(Cl)c23)CCN1/C(=N/C#N)Nc1cccc(Br)c1]

A. Preparation of 4,5-dichloro-7H-pyrrolo[2,3-d]pyrimidine

4-Chloro-pyrrolo[2,3-d]pyrimidine (0.5 g, 3.26 mmol) was suspended in anhydrous CH$_2$Cl$_2$ (25 ml), and N-chlorosuccinimide (0.87 g, 6.52 mmol) was added. The reaction mixture was refluxed for 3 days, then cooled to room temperature. The white solid was collected by filtration to give 5-dichloro-7H-pyrrolo[2,3-d]pyrimidine (0.54 g, 2.9 mmol, 88%).
$^1$H NMR (CD$_3$OD): δ 8.57 (1H, s), 7.60 (1H, s); MS (ES+) [M+H]$^+$=188.

Preparation of (S)—N-(3-bromophenyl)-4-(5-chloro-7H-pyrrolo[2,3-d]pyrimidin-4-yl)-N'-cyano-2-methylpiperazine-1-carboximidamide Using the pyrrolopyrimidine from step A, the title compound was prepared in the same manner as of (S)—N'-cyano-2-methyl-4-(5-methyl-7H-pyrrolo[2,3-d]pyrimidin-4-yl)-N-(3-(trifluoromethyl)phenyl)piperazine-1-carboximidamide from Example 8.
$^1$H NMR (CD$_3$OD): δ 8.29 (s, 1H), 7.12-7.34 (m, 5H), 4.64 (s, 1H), 4.41-4.43 (d, J=8 Hz, 1H), 4.16-4.19 (d, J=12 Hz, 1H), 3.98-4.02 (d, J=16 Hz, 1H), 3.71-3.78 (t, J=14 Hz, 1H), 3.47-3.52 (m, 1H), 3.21-3.28 (m, 1H), 1.35-1.36 (d, J=4 Hz, 3H); MS (ES+) [M+H]$^+$=475.

6.16. Example 16

(S)-4-(5-chloro-7H-pyrrolo[2,3-d]pyrimidin-4-yl)-N-(3-(isopropylcarbamoyl)phenyl)-2-methylpiperazine-1-carboxamide

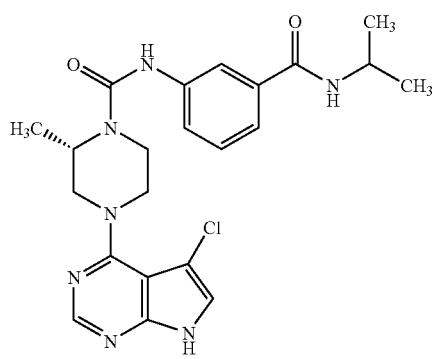 [SMILES: CC(C)NC(=O)c1cccc(NC(=O)N2CCN(c3ncnc4[nH]cc(Cl)c34)C[C@@H]2C)c1]

The title compound was prepared from 4,5-dichloro-7H-pyrrolo[2,3-d]pyrimidine, from Example 15, step A, in the same manner as (S)-3-(2-methyl-4-(5-methyl-7H-pyrrolo[2,3-d]pyrimidin-4-yl)piperazine-1-carboxamido)phenyl dimethylcarbamate from Example 2.

$^1$H NMR (CD$_3$OD): δ 8.28 (s, 1H), 7.81 (s, 1H), 7.36-7.54 (m, 3H), 7.31 (s, 1H), 4.57-4.59 (m, 1H), 4.43-4.46 (d, J=12 Hz, 1H), 4.18-4.24 (m, 2H), 4.04-4.08 (d, J=16 Hz, 1H), 3.62-3.68 (m, 1H), 3.44-3.48 (m, 1H), 3.19-3.23 (m, 1H), 1.33-1.38 (d, J=4 Hz, 3H), 1.26-1.27 (d, J=4 Hz, 6H). MS (ES+) [M+H]$^+$=456.

6.17. Example 17

N-(3-bromophenyl)-N'-cyano-2-methyl-4-(7H-pyrrolo[2,3-d]pyrimidin-4-yl)piperazine-1-carboximidamide

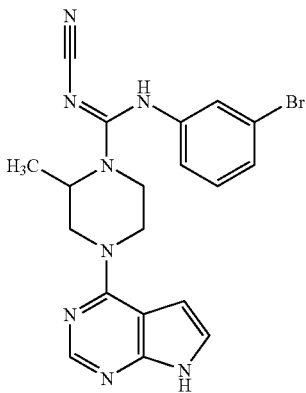 [SMILES: CC1CN(c2ncnc3[nH]ccc23)CCN1/C(=N/C#N)Nc1cccc(Br)c1]

The title compound was prepared from 4-chloro-7H-pyrrolo[2,3-d]pyrimidine by the same procedure as (S)—N'-cyano-2-methyl-4-(5-methyl-7H-pyrrolo[2,3-d]pyrimidin-4-yl)-N-(3-(trifluoromethyl)phenyl)piperazine-1-carboximidamide from Example 8.

$^1$H NMR (CD$_3$OD): δ 8.18 (s, 1H), 7.05-7.35 (m, 5H), 6.66 (s, 1H), 4.51-4.74 (m, 3H), 3.98-4.09 (m, 1H), 3.35-3.74 (m, 3H), 1.32-1.33 (d, J=4 Hz, 3H); MS (ES+) [M+H]$^+$=441.

6.18. Example 18

(S)-4-(5-cyano-7H-pyrrolo[2,3-d]pyrimidin-4-yl)-N-(3-(isopropylcarbamoyl)phenyl)-2-methylpiperazine-1-carboxamide

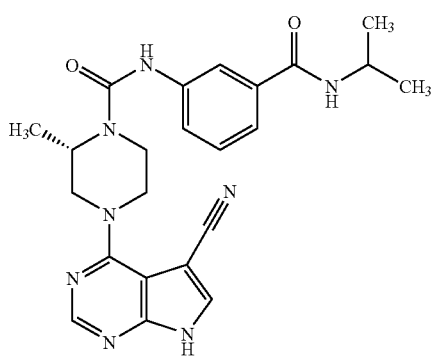 [SMILES: CC(C)NC(=O)c1cccc(NC(=O)N2CCN(c3ncnc4[nH]cc(C#N)c34)C[C@@H]2C)c1]

A. Preparation of 5-bromo-4-chloro-7H-pyrrolo[2,3-d]pyrimidine

To a solution of 4-chloro-7H-pyrrolo[2,3-d]pyrimidine (1.2 g, 7.8 mmol) in CH$_2$Cl$_2$ (25 ml) was added N-bromoacetamide (1.186 g, 8.6 mmol) in CH$_2$Cl$_2$ (25 ml). The mixture was heated at reflux temperature for 40 mins, then cooled to room temperature, and concentrated under vacuum to give an off-white solid. Cold water (40 ml) was added to the solid, which was then collected by filtration, washed with cold water (5 ml), and dried under vacuum. The product was recrystallized from a minimum amount of isopropanol to yield pure 5-bromo-4-chloro-7H-pyrrolo[2,3-d]pyrimidine (1.475 g, 81.5%).

$^1$H NMR (CD$_3$OD): δ 8.572 (s, 1H), 7.665 (s, 1H); MS (ES+) [M+H]$^+$=232.

B. Preparation of 5-bromo-4-chloro-7-(phenylsulfonyl)-7H-pyrrolo[2,3-d]pyrimidine To a slurry of 5-bromo-4-chloro-7H-pyrrolo[2,3-d]pyrimidine from step A (1.17 g, 5 mmol) in DMF (10 ml) at 0° C., was added NaH (60% in mineral oil, 0.28 g, 7 mmol). After stirring 15 min., benzensulfonyl chloride (0.64 ml, 5 mmol) was added. The reaction mixture was warmed to room temperature and stirred for 2 hours, resulting in precipitation of a white solid. More DMF (5 ml) was added, and the reaction was quenched with 10 ml of water. The solid was collected by filtration and dried in vacuum to afford 5-bromo-4-chloro-7-(phenylsulfonyl)-7H-pyrrolo[2,3-d]pyrimidine (1.62 g, 4.35 mmol, 87%) as a white solid, which was carried on without further purification. MS (ES+) [M+H]$^+$=373.

C. Preparation of (S)-5-bromo-4-(3-methylpiperazin-1-yl)-7-(phenylsulfonyl)-7H-pyrrolo[2,3-d]pyrimidine To a mixture of pyrrolopyrimidine from step B (76 mg, 0.2 mmol) and (S)-2-methylpiperazine (21 mg, 0.2 mmol) in isopropanol (2 ml) was added triethylamine (0.11 ml, 0.8 mmol). The mixture was heated at 80° C. for 5 mins via microwave and concentrated under vacuum to give crude (S)-5-bromo-4-(3-methylpiperazin-1-yl)-7-(phenylsulfonyl)-7H-pyrrolo[2,3-d]pyrimidine (65 mg, 0.15 mmol, 75%) which was used directly for the next step. MS (ES+) [M+H]$^+$=437.

D. Preparation of (S)-4-(5-bromo-7-(phenylsulfonyl)-7H-pyrrolo[2,3-d]pyrimidin-4-yl)-N-(3-(isopropylcarbamoyl)phenyl)-2-methylpiperazine-1-carboxamide To a solution of triphosgene (15 mg, 0.05 mmol) in THF (1 ml) at 0° C. under N$_2$ was added dropwise a solution of 3-amino-N-isopropylbenzamide (25 mg, 0.14 mmol) and triethylamine (43 μL, 0.3 mmol) in THF (1 ml). The mixture was stirred for 15 min at 0° C. and another 15 min at room temperature. The piperazine from step C (65 mg, 0.14 mmol) in THF (1 ml) was added, and the resulting mixture was stirred at room temperature overnight, then quenched with MeOH and K$_2$CO$_3$ (97 mg, 0.70 mmol) and filtered. The solution was concentrated under vacuum and purified by Prep-HPLC to give (S)-4-(5-bromo-7-(phenylsulfonyl)-7H-pyrrolo[2,3-d]pyrimidin-4-yl)-N-(3-(isopropylcarbamoyl)phenyl)-2-methylpiperazine-1-carboxamide (70 mg, 0.11 mmol, 77%). MS (ES+) [M+H]$^+$=641.

E. Preparation of (S)-4-(5-cyano-7H-pyrrolo[2,3-d]pyrimidin-4-yl)-N-(3-(isopropylcarbamoyl)phenyl)-2-methylpiperazine-1-carboxamide To a solution of (S)-4-(5-bromo-7-(phenylsulfonyl)-7H-pyrrolo[2,3-d]pyrimidin-4-yl)-N-(3-(isopropylcarbamoyl)phenyl)-2-methylpiperazine-1-carboxamide from step D (70 mg, 0.11 mmol) in DMF (2 ml) was added Zn(CN)$_2$ (26 mg, 0.22 mmol) and Pd(PPh$_3$)$_4$ (13 mg, 0.011 mmol). The mixture was heated at 150° C. for 3 min via microwave, cooled to room temperature, and filtered through a pad of celite. The solution was concentrated under vacuum, and the residue was treated with NaOH and MeOH for 2 hrs. The product was purified by Prep-HPLC to obtain (S)-4-(5-cyano-7H-pyrrolo[2,3-d]pyrimidin-4-yl)-N-(3-(isopropylcarbamoyl)phenyl)-2-methylpiperazine-1-carboxamide as a white solid.

$^1$H NMR (CD$_3$OD): δ 8.37 (s, 1H), 8.07 (s, 1H), 7.79 (s, 1H), 7.32-7.61 (m, 3H), 4.52-4.65 (m, 2H), 4.30-4.42 (m, 1H), 4.18-4.16 (m, 1H), 4.02-4.13 (m, 1H), 3.57-3.76 (m, 2H), 3.38-3.47 (m, 1H), 1.31-1.33 (d, J=8 Hz, 3H), 1.26-1.28 (d, J=8 Hz, 6H); MS (ES+) [M+H]$^+$=447.

6.19. Example 19

(S)—N-(3-bromophenyl)-2-methyl-4-(5-methyl-7H-pyrrolo[2,3-d]pyrimidin-4-yl)-N'-(methylsulfonyl)piperazine-1-carboximidamide

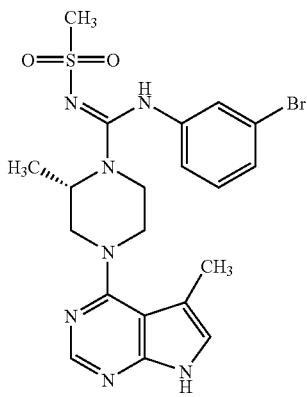 [SMILES: Cc1c[nH]c2ncnc(N3CCN(/C(=N/S(N)(=O)=O)Nc4cccc(Br)c4)[C@@H](C)C3)c12]

A. Preparation of diphenyl methylsulfonylcarbonimidate

Dichlorodiphenoxymethane (2 g, 7.46 mmol) and methylsulfonamide (1.56 g, 16.41 mmol) were dissolved in EtOAc (15 ml) and heated to reflux for 12 hours. The mixture was allowed to cool and was concentrated under vacuum. Purification of the crude mixture by flash chromatography (20% EtOAc/hexanes) afforded diphenyl methylsulfonylcarbonimidate (0.75 g, 2.59 mmol, 35%).

$^1$H NMR (400 MHz, chloroform) δ ppm 7.38-7.43 (m, 4H), 7.30 (m, 2H), 7.21 (m, 4H), 3.01 (s, 3H); MS (ES+) [M+H]$^+$= 292.

B. Preparation of phenyl N-3-bromophenyl-N'-(methylsulfonyl)carbamimidate

Diphenyl methylsulfonylcarbonimidate from step A (0.75 g, 2.59 mmol) and 3-bromoaniline (0.28 ml, 2.59 mmol) were dissolved in acetonitrile (5 ml) and heated to 70° C. for 12 hours. The reaction was cooled to room temperature and concentrated under vacuum. Purification by flash chromatography (30% EtOAc/hexanes) afforded phenyl N-3-bromophenyl-N'-(methylsulfonyl)carbamimidate (0.50 g, 1.35 mmol, 52%).

$^1$H NMR (400 MHz, chloroform) δ ppm 9.25 (s, 1H), 7.54 (m, 1H), 7.40 (m, 3H), 7.26 (m, 2H), 7.13 (m, 2H), 2.96 (s, 3H); MS (ES+) [M+H]$^+$=369, 371.

C. Preparation of (S)—N-(3-bromophenyl)-2-methyl-4-(5-methyl-7H-pyrrolo[2,3-d]pyrimidin-4-yl)-N'-(methylsulfonyl)piperazine-1-carboximidamide The carbamimidate from step B (100 mg, 0.27 mmol), (S)-5-methyl-4-(3-methylpiperazin-1-yl)-7H-pyrrolo[2,3-d]pyrimidine, from Example 1, step B (63 mg, 0.27 mmol), and triethylamine (77 µl, 0.27 mmol) were combined in MeCN (1.5 ml) and heated to reflux for 2 hours. The mixture was concentrated and purified by preparative HPLC to afford (S)—N-(3-bromophenyl)-2-methyl-4-(5-methyl-7H-pyrrolo[2,3-d]pyrimidin-4-yl)-N'-(methylsulfonyl)piperazine-1-carboximidamide.

$^1$H NMR (400 MHz, methanol) δ ppm 8.19 (s, 1H), 7.40 (s, 1H), 7.30 (m, 2H), 7.16 (m, 1H), 7.01 (s, 1H), 4.46 (m, 1H), 4.01 (m, 1H), 3.78 (m, 2H), 3.52 (m, 1H), 3.40 (m, 1H), 3.08 (m, 1H), 2.98 (s, 3H), 2.39 (d, J=1.0 Hz, 3H), 1.26 (d, J=6.8 Hz, 3H); MS (ES+) [M+H]$^+$=506, 508.

6.20. Example 20

(S)—N-(3-bromophenyl)-2-methyl-4-(5-methyl-7H-pyrrolo[2,3-d]pyrimidin-4-yl)-N'-sulfamoylpiperazine-1-carboximidamide

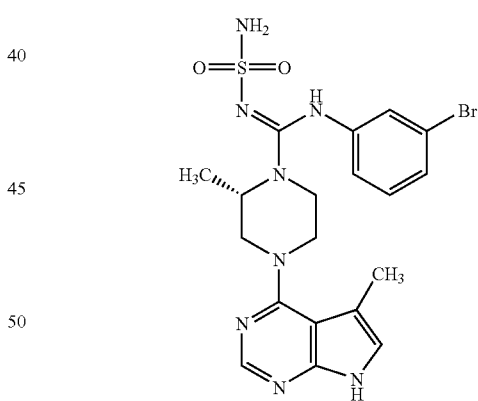

A. Preparation of diphenyl sulfamoylcarbonimidate

Dichlorodiphenoxymethane (1 g, 3.72 mmol) and sulfamide (0.72 g, 7.44 mmol) were dissolved in MeCN (10 ml) and stirred at room temperature for 18 hours. The mixture was concentrated under vacuum and purified by flash chromatography (20-40% EtOAc/hexanes) to afford diphenyl sulfamoylcarbonimidate (0.69 g, 2.34 mmol, 63%) as a colorless oil.

$^1$H NMR (400 MHz, methanol) δ ppm 7.43-7.47 (m, 4H), 7.24-7.33 (m, 6H); MS (ES+) [M+H]$^+$=293.

B. Preparation of phenyl N-3-bromophenyl-N'-sulfamoylcarbamimidate

Diphenyl sulfamoylcarbonimidate, from step A, (0.05 g, 0.17 mmol) and 3-bromoaniline (18 μl, 0.17 mmol) were dissolved in acetonitrile (0.5 ml) and heated to 70° C. for 12 hours. The reaction was concentrated under vacuum to afford phenyl N-3-bromophenyl-N'-sulfamoylcarbamimidate, which was carried on crude to the next reaction.

C. Preparation of (S)—N-(3-bromophenyl)-2-methyl-4-(5-methyl-7H-pyrrolo[2,3-d]pyrimidin-4-yl)-N'-sulfamoylpiperazine-1-carboximidamide Crude carbamimidate from step B (~25 mg, 0.068 mmol), (S)-5-methyl-4-(3-methylpiperazin-1-yl)-7H-pyrrolo[2,3-d]pyrimidine, from Example 1, step B (16 mg, 0.68 mmol), and triethylamine (10 μl, 0.068 mmol) were combined in MeCN (0.5 ml) and heated to 70° C. for 2 hours. The mixture was concentrated and purified by preparative HPLC to afford (S)—N-(3-bromophenyl)-2-methyl-4-(5-methyl-7H-pyrrolo[2,3-d]pyrimidin-4-yl)-N'-sulfamoylpiperazine-1-carboximidamide (4 mg, 0.0075 mmol, 11%) as a white solid.

$^1$H NMR (400 MHz, methanol) δ ppm 8.19 (s, 1H), 7.31 (m, 1H), 7.20 (m, 1H), 7.11-7.15 (m, 2H), 7.07 (m, 1H), 4.43 (m, 1H), 4.03 (m, 1H), 3.76 (m, 2H), 3.47 (m, 1H), 3.35 (m, 1H), 3.05 (m, 1H), 2.39 (d, J=1.0 Hz, 3H), 1.25 (d, J=6.8 Hz, 3H); MS (ES+) [M+H]$^+$=507, 509.

6.21. Example 21

(S)—N-(3-bromophenyl)-N'—(N-((dimethylamino)methylene)sulfamoyl)-2-methyl-4-(5-methyl-7H-pyrrolo[2,3-d]pyrimidin-4-yl)piperazine-1-carboximidamide

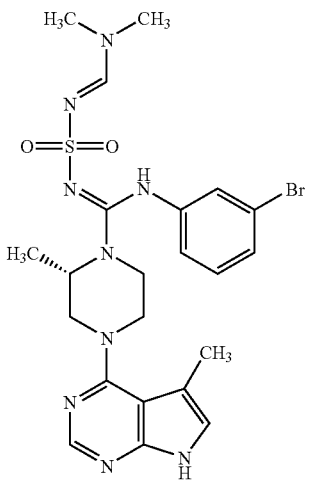 [SMILES: Cc1c[nH]c2ncnc(N3CCN(/C(=N/S(=O)(=O)/N=C/N(C)C)Nc4cccc(Br)c4)[C@@H](C)C3)c12]

Crude (S)—N-(3-bromophenyl)-2-methyl-4-(5-methyl-7H-pyrrolo[2,3-d]pyrimidin-4-yl)-N'-sulfamoylpiperazine-1-carboximidamide from Example 20, step C, (~25 mg, 0.068 mmol) was dissolved in MeOH (0.5 ml) and N,N-dimethylformamide dimethyl acetal (7 μl) added. The mixture was stirred at room temperature for 20 minutes and then concentrated. The mixture was purified by preparative HPLC to afford the desired compound (5 mg, 0.0088 mmol, 13%) as a white solid.

$^1$H NMR (400 MHz, methanol) δ ppm 8.19 (s, 1H), 8.02 (s, 1H), 7.28 (m, 2H), 7.10 (m, 2H), 7.01 (s, 1H), 4.48 (m, 1H), 4.03 (m, 1H), 3.79 (m, 2H), 3.49 (m, 1H), 3.36 (m, 1H), 3.05 (m, 1H), 2.97 (s, 3H), 2.86 (s, 3H), 2.39 (d, J=1.0 Hz, 3H), 1.25 (d, J=6.8 Hz, 3H); MS (ES+) [M+H]$^+$=562, 564.

6.22. Example 22

4-fluoro-N-(3-(2-(4-(5-methyl-7H-pyrrolo[2,3-d]pyrimidin-4-yl)piperazin-1-yl)-2-oxoethyl)phenyl)benzamide

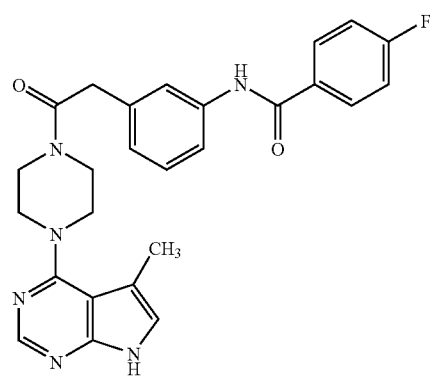 [SMILES: Cc1c[nH]c2ncnc(N3CCN(C(=O)Cc4cccc(NC(=O)c5ccc(F)cc5)c4)CC3)c12]

A. Preparation of 2-(3-nitrophenyl)-1-(piperazin-1-yl)ethanone 2-(3-nitrophenyl)acetyl chloride (0.20 ml, 1.0 mmol.) was added to a vigorously stirred mixture of tert-butyl piperazine-1-carboxylate (0.19 g, 1.0 mmol.) in CH$_2$Cl$_2$ (2 ml) and sat. aq. NaHCO$_3$ (1 ml). The reaction was stirred for 1 hour; then the organic layer was separated, filtered through a plug of MgSO$_4$, and concentrated under vacuum. The residue was treated with TFA in CH$_2$Cl$_2$ to remove the Boc group to give 2-(3-nitrophenyl)-1-(piperazin-1-yl)ethanone, which was carried on crude.

B. Preparation of 1-(4-(5-methyl-7H-pyrrolo[2,3-d]pyrimidin-4-yl)piperazin-1-yl)-2-(3-nitrophenyl)ethanone 2-(3-Nitrophenyl)-1-(piperazin-1-yl)ethanone from step A (0.32 g, 0.9 mmol), 4-chloro-5-methyl-7H-pyrrolo[2,3-d]pyrimidine (0.168 g, 1.0 mmol), and diisopropylethylamine (0.1 ml) were combined in isopropanol and heated at 80° C. for 24 hours. The product was isolated by prep HPLC to give 1-(4-(5-methyl-7H-pyrrolo[2,3-d]pyrimidin-4-yl)piperazin-1-yl)-2-(3-nitrophenyl)ethanone.

C. Preparation of 4-fluoro-N-(3-(2-(4-(5-methyl-7H-pyrrolo[2,3-d]pyrimidin-4-yl)piperazin-1-yl)-2-oxoethyl)phenyl)benzamide To a solution of 1-(4-(5-methyl-7H-pyrrolo[2,3-d]pyrimidin-4-yl)piperazin-1-yl)-2-(3-nitrophenyl)ethanone from step B (0.13 g, 0.3 mmol.) in isopropanol (2 ml) was added SnCl$_2$ (0.19 g, 1 mmol.) and 1 drop of concentrated aq. HCl. The reaction was heated at reflux for 2 hours, and the aniline product was isolated by standard procedures. A portion of his material (35 mg, 0.1 mmol.) was dissolved in CH$_2$Cl$_2$ (2 mL) and sat. aq. NaHCO$_3$ (2 ml). 4-Fluorobenzoyl chloride (16 mg, 0.1 mmol.) in CH$_2$Cl$_2$ (1 mL) was added dropwise with vigorous stirring. The reaction was stirred for 2 hours, then worked up by standard procedures. The product was isolated by prep HPLC followed by prep TLC to afford 4-fluoro-N-(3-(2-(4-(5-methyl-7H-pyrrolo[2,3-d]pyrimidin-4-yl)piperazin-1-yl)-2-oxoethyl)phenyl)benzamide. MS (ES+) [M+H]$^+$=473.

6.23. Additional Compounds

Additional compounds were prepared using methods described herein and known in the art. Some of those compounds are listed below with their observed masses.

TABLE 1

| Compound | (M + H)$^+$ |
|---|---|
| (2S)—N-(bicyclo[2.2.1]heptan-2-yl)-N'-cyano-2-methyl-4-(5-methyl-7H-pyrrolo[2,3-d]pyrimidin-4-yl)piperazine-1-carboximidamide | 393.2 |
| (3-{[(S)-2-Methyl-4-(5-methyl-7H-pyrrolo[2,3-d]pyrimidin-4-yl)-piperazine-1-carbonyl]-amino}-phenyl)-carbamic acid isobutyl ester | 466 |
| (3-Bromo-phenylamino)-[(R)-2-tert-butoxymethyl-4-(5-methyl-7H-pyrrolo[2,3-d]pyrimidin-4-yl)-piperazin-1-yl]-methyl-cyanamide | 528 |
| (R)-2-Methyl-4-(5-methyl-7H-pyrrolo[2,3-d]pyrimidin-4-yl)-piperazine-1-carboxylic acid (3-bromo-phenyl)-amide | 431 |
| (R)—N-(3-bromophenyl)-N'-cyano-2-(hydroxymethyl)-4-(5-methyl-7H-pyrrolo[2,3-d]pyrimidin-4-yl)piperazine-1-carboximidamide | 470 |
| (S)-2-Methyl-4-(5-methyl-7H-pyrrolo[2,3-d]pyrimidin-4-yl)-piperazine-1-carboxylic acid (3-bromo-phenyl)-amide | 429; 431 |
| (S)-2-Methyl-4-(5-methyl-7H-pyrrolo[2,3-d]pyrimidin-4-yl)-piperazine-1-carboxylic acid [3-(4-fluoro-phenoxy)-phenyl]-amide | 461 |
| (S)-2-Methyl-4-(5-methyl-7H-pyrrolo[2,3-d]pyrimidin-4-yl)-piperazine-1-carboxylic acid (3-chloro-phenyl)-amide | 385 |
| (S)-2-Methyl-4-(5-methyl-7H-pyrrolo[2,3-d]pyrimidin-4-yl)-piperazine-1-carboxylic acid (3-fluoro-phenyl)-amide | 369 |
| (S)-2-Methyl-4-(5-methyl-7H-pyrrolo[2,3-d]pyrimidin-4-yl)-piperazine-1-carboxylic acid (3-cyano-phenyl)-amide | 376 |
| (S)-2-Methyl-4-(5-methyl-7H-pyrrolo[2,3-d]pyrimidin-4-yl)-piperazine-1-carboxylic acid (2-bromo-phenyl)-amide | 429, 431 |
| (S)-2-Methyl-4-(5-methyl-7H-pyrrolo[2,3-d]pyrimidin-4-yl)-piperazine-1-carboxylic acid o-tolylamide | 365 |
| (S)-2-Methyl-4-(5-methyl-7H-pyrrolo[2,3-d]pyrimidin-4-yl)-piperazine-1-carboxylic acid (4-bromo-phenyl)-amide | 431 |
| (S)-2-Methyl-4-(5-methyl-7H-pyrrolo[2,3-d]pyrimidin-4-yl)-piperazine-1-carboxylic acid m-tolylamide | 365 |
| (S)-2-Methyl-4-(5-methyl-7H-pyrrolo[2,3-d]pyrimidin-4-yl)-piperazine-1-carboxylic acid [3-(morpholine-4-carbonyl)-phenyl]-amide | 464.2 |
| (S)-2-Methyl-4-(5-methyl-7H-pyrrolo[2,3-d]pyrimidin-4-yl)-piperazine-1-carboxylic acid [3-(2-dimethylamino-ethylcarbamoyl)-phenyl]-amide | 465 |
| (S)-2-Methyl-4-(5-methyl-7H-pyrrolo[2,3-d]pyrimidin-4-yl)-piperazine-1-carboxylic acid (3-isopropylcarbamoyl-phenyl)-amide | 436 |
| (S)-2-Methyl-4-(5-methyl-7H-pyrrolo[2,3-d]pyrimidin-4-yl)-piperazine-1-carboxylic acid (3-isopropylsulfamoyl-phenyl)-amide | 472 |
| (S)-2-Methyl-4-(5-methyl-7H-pyrrolo[2,3-d]pyrimidin-4-yl)-piperazine-1-carboxylic acid [3-(2-hydroxy-ethylcarbamoyl)-phenyl]-amide | 438.1 |
| (S)-2-Methyl-4-(5-methyl-7H-pyrrolo[2,3-d]pyrimidin-4-yl)-piperazine-1-carboxylic acid [3-(1-methyl-piperidin-4-ylsulfamoyl)-phenyl]-amide | 527.1 |
| (S)-2-Methyl-4-(5-methyl-7H-pyrrolo[2,3-d]pyrimidin-4-yl)-piperazine-1-carboxylic acid (3-methoxy-phenyl)-amide | 381 |
| (S)-2-Methyl-4-(5-methyl-7H-pyrrolo[2,3-d]pyrimidin-4-yl)-piperazine-1-carboxylic acid [3-((S)-2-hydroxy-1-methyl-ethylcarbamoyl)-phenyl]-amide | 452.3 |
| (S)-2-Methyl-4-(5-methyl-7H-pyrrolo[2,3-d]pyrimidin-4-yl)-piperazine-1-carboxylic acid [3-((R)-2-hydroxy-1-methyl-ethylcarbamoyl)-phenyl]-amide | 452.2 |
| (S)-2-Methyl-4-(5-methyl-7H-pyrrolo[2,3-d]pyrimidin-4-yl)-piperazine-1-carboxylic acid (3-cyclopropylsulfamoyl-phenyl)-amide | 470.1 |
| (S)-2-Methyl-4-(5-methyl-7H-pyrrolo[2,3-d]pyrimidin-4-yl)-piperazine-1-carboxylic acid [3-(2-hydroxy-1-hydroxymethyl-ethylcarbamoyl)-phenyl]-amide | 468 |
| (S)-2-Methyl-4-(5-methyl-7H-pyrrolo[2,3-d]pyrimidin-4-yl)-piperazine-1-carboxylic acid (3-cyclopropylcarbamoyl-phenyl)-amide | 434 |
| (S)-2-Methyl-4-(5-methyl-7H-pyrrolo[2,3-d]pyrimidin-4-yl)-piperazine-1-carboxylic acid (3-dimethylcarbamoylmethoxy-phenyl)-amide | 452 |
| (S)-2-Methyl-4-(5-methyl-7H-pyrrolo[2,3-d]pyrimidin-4-yl)-piperazine-1-carboxylic acid [3-(1-methyl-piperidin-4-ylcarbamoyl)-phenyl]-amide | 491.1 |
| (S)-2-Methyl-4-(5-methyl-7H-pyrrolo[2,3-d]pyrimidin-4-yl)-piperazine-1-carboxylic acid (3-isopropoxy-phenyl)-amide | 409 |
| (S)-2-Methyl-4-(5-methyl-7H-pyrrolo[2,3-d]pyrimidin-4-yl)-piperazine-1-carboxylic acid [3-(2-dimethylamino-ethoxy)-phenyl]-amide | 438 |
| (S)-2-Methyl-4-(5-methyl-7H-pyrrolo[2,3-d]pyrimidin-4-yl)-piperazine-1-carboxylic acid [3-(2-hydroxy-1-hydroxymethyl-ethylsulfamoyl)-phenyl]-amide | 504.1 |
| (S)-2-Methyl-4-(5-methyl-7H-pyrrolo[2,3-d]pyrimidin-4-yl)-piperazine-1-carboxylic acid [3-(3-dimethylamino-propionylamino)-phenyl]-amide | 465 |
| (S)-2-Methyl-4-(5-methyl-7H-pyrrolo[2,3-d]pyrimidin-4-yl)-piperazine-1-carboxylic acid [3-(3-methyl-butyrylamino)-phenyl]-amide | 450 |

TABLE 1-continued

| Compound | (M + H)+ |
|---|---|
| (S)-2-Methyl-4-(5-methyl-7H-pyrrolo[2,3-d]pyrimidin-4-yl)-piperazine-1-carboxylic acid {3-[(tetrahydro-furan-2-carbonyl)-amino]-phenyl}-amide | 464 |
| (S)-2-Methyl-4-(5-methyl-7H-pyrrolo[2,3-d]pyrimidin-4-yl)-piperazine-1-carboxylic acid [3-(4-dimethylamino-butyrylamino)-phenyl]-amide | 479 |
| (S)-2-Methyl-4-(5-methyl-7H-pyrrolo[2,3-d]pyrimidin-4-yl)-piperazine-1-carboxylic acid {3-[2-(3-butyl-ureido)-acetylamino]-phenyl}-amide | 522 |
| (S)-2-Methyl-4-(5-methyl-7H-pyrrolo[2,3-d]pyrimidin-4-yl)-piperazine-1-carboxylic acid {3-[(furan-2-carbonyl)-amino]-phenyl}-amide | 460 |
| (S)-2-Methyl-4-(5-methyl-7H-pyrrolo[2,3-d]pyrimidin-4-yl)-piperazine-1-carboxylic acid {3-[2-(pyridin-4-ylsulfanyl)-acetylamino]-phenyl}-amide | 517 |
| (S)-2-Methyl-4-(5-methyl-7H-pyrrolo[2,3-d]pyrimidin-4-yl)-piperazine-1-carboxylic acid [3-(2-amino-acetylamino)-phenyl]-amide | 423 |
| (S)-2-Methyl-4-(5-methyl-7H-pyrrolo[2,3-d]pyrimidin-4-yl)-piperazine-1-carboxylic acid (4-methoxy-phenyl)-amide | 381 |
| (S)-2-Methyl-4-(5-methyl-7H-pyrrolo[2,3-d]pyrimidin-4-yl)-piperazine-1-carboxylic acid [4-(2-dimethylamino-ethylcarbamoyl)-phenyl]-amide | 465 |
| (S)-2-Methyl-4-(5-methyl-7H-pyrrolo[2,3-d]pyrimidin-4-yl)-piperazine-1-carboxylic acid {3-[(4-methyl-piperazine-1-carbonyl)-amino]-phenyl}-amide | 492 |
| (S)-2-Methyl-4-(5-methyl-7H-pyrrolo[2,3-d]pyrimidin-4-yl)-piperazine-1-carboxylic acid (4-ethylcarbamoyl-phenyl)-amide | 422 |
| (S)-2-Methyl-4-(5-methyl-7H-pyrrolo[2,3-d]pyrimidin-4-yl)-piperazine-1-carboxylic acid [4-(2-hydroxy-ethylcarbamoyl)-phenyl]-amide | 438 |
| (S)-2-Methyl-4-(5-methyl-7H-pyrrolo[2,3-d]pyrimidin-4-yl)-piperazine-1-carboxylic acid {3-[3-(4-chloro-butyl)-3-methyl-ureido]-phenyl}-amide | 514 |
| (S)-2-Methyl-4-(5-methyl-7H-pyrrolo[2,3-d]pyrimidin-4-yl)-piperazine-1-carboxylic acid (4-carbamoyl-phenyl)-amide | 394 |
| (S)-2-Methyl-4-(5-methyl-7H-pyrrolo[2,3-d]pyrimidin-4-yl)-piperazine-1-carboxylic acid [4-(3-dimethylamino-propionylamino)-phenyl]-amide | 465 |
| (S)-2-Methyl-4-(5-methyl-7H-pyrrolo[2,3-d]pyrimidin-4-yl)-piperazine-1-carboxylic acid (3-aminomethyl-phenyl)-amide | 380.1 |
| (S)-2-Methyl-4-(5-methyl-7H-pyrrolo[2,3-d]pyrimidin-4-yl)-piperazine-1-carboxylic acid (4-aminomethyl-phenyl)-amide | 380.2 |
| (S)-2-Methyl-4-(5-methyl-7H-pyrrolo[2,3-d]pyrimidin-4-yl)-piperazine-1-carboxylic acid (3-dimethylaminomethyl-phenyl)-amide | 408.3 |
| (S)-2-Methyl-4-(5-methyl-7H-pyrrolo[2,3-d]pyrimidin-4-yl)-piperazine-1-carboxylic acid [4-(3,3-dimethyl-ureido)-phenyl]-amide | 437 |
| (S)-2-Methyl-4-(5-methyl-7H-pyrrolo[2,3-d]pyrimidin-4-yl)-piperazine-1-carboxylic acid {3-[((S)-2-oxo-thiazolidine-4-carbonyl)-amino]-phenyl}-amide | 495 |
| (S)-2-Methyl-4-(5-methyl-7H-pyrrolo[2,3-d]pyrimidin-4-yl)-piperazine-1-carboxylic acid pyridin-3-ylamide | 352.1 |
| (S)-2-Methyl-4-(5-methyl-7H-pyrrolo[2,3-d]pyrimidin-4-yl)-piperazine-1-carboxylic acid pyridin-4-ylamide | 352.2 |
| (S)-2-Methyl-4-(5-methyl-7H-pyrrolo[2,3-d]pyrimidin-4-yl)-piperazine-1-carboxylic acid thiazol-2-ylamide | 358.2 |
| (S)-3-(N'-cyano-2-methyl-4-(5-methyl-7H-pyrrolo[2,3-d]pyrimidin-4-yl)piperazine-1-carboximidamido)-N-isopropylbenzamide | 460.1 |
| (S)-3-(N'-cyano-2-methyl-4-(5-methyl-7H-pyrrolo[2,3-d]pyrimidin-4-yl)piperazine-1-carboximidamido)benzoic acid | 419.1 |
| (S)-3-(N'-cyano-2-methyl-4-(5-methyl-7H-pyrrolo[2,3-d]pyrimidin-4-yl)piperazine-1-carboximidamido)-N-ethylbenzamide | 446.1 |
| (S)-3-(N'-cyano-2-methyl-4-(5-methyl-7H-pyrrolo[2,3-d]pyrimidin-4-yl)piperazine-1-carboximidamido)-N-(2-hydroxyethyl)benzamide | 462.1 |
| (S)-3-(N'-cyano-2-methyl-4-(5-methyl-7H-pyrrolo[2,3-d]pyrimidin-4-yl)piperazine-1-carboximidamido)-N-(2-(dimethylamino)ethyl)benzamide | 489.2 |
| (S)-3-(N'-cyano-2-methyl-4-(5-methyl-7H-pyrrolo[2,3-d]pyrimidin-4-yl)piperazine-1-carboximidamido)-N-(2-morpholinoethyl)benzamide | 531.1 |
| (S)-3-(N'-cyano-2-methyl-4-(5-methyl-7H-pyrrolo[2,3-d]pyrimidin-4-yl)piperazine-1-carboximidamido)-N-(2-(pyrrolidin-1-yl)ethyl)benzamide | 515.1 |
| (S)-4-(N'-cyano-2-methyl-4-(5-methyl-7H-pyrrolo[2,3-d]pyrimidin-4-yl)piperazine-1-carboximidamido)benzamide | 418 |
| (S)-5-(N'-cyano-2-methyl-4-(5-methyl-7H-pyrrolo[2,3-d]pyrimidin-4-yl)piperazine-1-carboximidamido)-2-fluoro-N-(2-hydroxyethyl)benzamide | 480 |
| (S)-methyl 3-(N'-cyano-2-methyl-4-(5-methyl-7H-pyrrolo[2,3-d]pyrimidin-4-yl)piperazine-1-carboximidamido)benzoate | 433.1 |
| (S)—N-((trans)-4-aminocyclohexyl)-N'-cyano-2-methyl-4-(5-methyl-7H-pyrrolo[2,3-d]pyrimidin-4-yl)piperazine-1-carboximidamide | 396.3 |
| (S)—N-(3-tert-butylphenyl)-N'-cyano-2-methyl-4-(5-methyl-7H-pyrrolo[2,3-d]pyrimidin-4-yl)piperazine-1-carboximidamide | 431.2 |
| (S)—N-adamantyl-N'-cyano-2-methyl-4-(5-methyl-7H-pyrrolo[2,3-d]pyrimidin-4-yl)piperazine-1-carboximidamide | 433.2 |
| (S)—N-benzyl-N'-cyano-2-methyl-4-(5-methyl-7H-pyrrolo[2,3-d]pyrimidin-4-yl)piperazine-1-carboximidamide | 389.1 |
| (S)—N'-cyano-2-methyl-4-(5-methyl-7H-pyrrolo[2,3-d]pyrimidin-4-yl)-N-(3-(trifluoromethyl)phenyl)piperazine-1-carboximidamide | 443 |
| (S)—N'-cyano-2-methyl-4-(5-methyl-7H-pyrrolo[2,3-d]pyrimidin-4-yl)-N-(3-(methylthio)phenyl)piperazine-1-carboximidamide | 421 |
| (S)—N'-cyano-2-methyl-4-(5-methyl-7H-pyrrolo[2,3-d]pyrimidin-4-yl)-N-(pyridin-3-yl)piperazine-1-carboximidamide | 376.2 |

TABLE 1-continued

| Compound | (M + H)+ |
|---|---|
| (S)—N'-cyano-2-methyl-4-(5-methyl-7H-pyrrolo[2,3-d]pyrimidin-4-yl)-N-p-tolylpiperazine-1-carboximidamide | 389.2 |
| (S)—N'-cyano-2-methyl-4-(5-methyl-7H-pyrrolo[2,3-d]pyrimidin-4-yl)-N-(4-methylcyclohexyl)piperazine-1-carboximidamide | 395.2 |
| (S)—N'-cyano-2-methyl-4-(5-methyl-7H-pyrrolo[2,3-d]pyrimidin-4-yl)-N-(piperidin-4-yl)piperazine-1-carboximidamide | 382 |
| (S)—N'-cyano-2-methyl-4-(5-methyl-7H-pyrrolo[2,3-d]pyrimidin-4-yl)-N-(pyridin-2-ylmethyl)piperazine-1-carboximidamide | 390 |
| (S)—N'-cyano-2-methyl-4-(5-methyl-7H-pyrrolo[2,3-d]pyrimidin-4-yl)-N-(1-methylpiperidin-4-yl)piperazine-1-carboximidamide | 396 |
| (S)—N'-cyano-2-methyl-4-(5-methyl-7H-pyrrolo[2,3-d]pyrimidin-4-yl)-N-phenylpiperazine-1-carboximidamide | 375 |
| (S)—N'-cyano-2-methyl-4-(5-methyl-7H-pyrrolo[2,3-d]pyrimidin-4-yl)-N-(3-(morpholine-4-carbonyl)phenyl)piperazine-1-carboximidamide | 488.2 |
| (S)—N'-cyano-2-methyl-4-(5-methyl-7H-pyrrolo[2,3-d]pyrimidin-4-yl)-N-(3-(N-(2-morpholinoethyl)sulfamoyl)phenyl)piperazine-1-carboximidamide | 567.2 |
| (S)—N'-cyano-2-methyl-4-(5-methyl-7H-pyrrolo[2,3-d]pyrimidin-4-yl)-N-(3-(N-(1-methylpiperidin-4-yl)sulfamoyl)phenyl)piperazine-1-carboximidamide | 551.1 |
| (S)—N'-cyano-2-methyl-4-(5-methyl-7H-pyrrolo[2,3-d]pyrimidin-4-yl)-N-(tetrahydro-2H-pyran-4-yl)piperazine-1-carboximidamide | 383.1 |
| (S)—N'-cyano-2-methyl-4-(5-methyl-7H-pyrrolo[2,3-d]pyrimidin-4-yl)-N-(3-oxo-1,3-dihydroisobenzofuran-5-yl)piperazine-1-carboximidamide | 431 |
| (S)—N'-cyano-2-methyl-4-(5-methyl-7H-pyrrolo[2,3-d]pyrimidin-4-yl)-N-(pyridin-4-ylmethyl)piperazine-1-carboximidamide | 390.1 |
| (S)—N'-cyano-2-methyl-4-(5-methyl-7H-pyrrolo[2,3-d]pyrimidin-4-yl)-N-(pyridin-3-ylmethyl)piperazine-1-carboximidamide | 390.2 |
| (S)—N'-cyano-N-((trans)-4-hydroxycyclohexyl)-2-methyl-4-(5-methyl-7H-pyrrolo[2,3-d]pyrimidin-4-yl)piperazine-1-carboximidamide | 397.1 |
| (S)—N'-cyano-N-(3-((dimethylamino)methyl)phenyl)-2-methyl-4-(5-methyl-7H-pyrrolo[2,3-d]pyrimidin-4-yl)piperazine-1-carboximidamide | 432.3 |
| (S)—N'-cyano-N-(3-(4-fluorophenoxy)phenyl)-2-methyl-4-(5-methyl-7H-pyrrolo[2,3-d]pyrimidin-4-yl)piperazine-1-carboximidamide | 485.1 |
| (S)—N'-cyano-N-(3-(N-(2-(dimethylamino)ethyl)sulfamoyl)phenyl)-2-methyl-4-(5-methyl-7H-pyrrolo[2,3-d]pyrimidin-4-yl)piperazine-1-carboximidamide | 525.1 |
| (S)—N'-cyano-N-(3-(N-(2-hydroxyethyl)sulfamoyl)phenyl)-2-methyl-4-(5-methyl-7H-pyrrolo[2,3-d]pyrimidin-4-yl)piperazine-1-carboximidamide | 498.1 |
| (S)—N'-cyano-N-(3-(N-isopropylsulfamoyl)phenyl)-2-methyl-4-(5-methyl-7H-pyrrolo[2,3-d]pyrimidin-4-yl)piperazine-1-carboximidamide | 496.1 |
| (S)—N'-cyano-N-(3-cyanophenyl)-2-methyl-4-(5-methyl-7H-pyrrolo[2,3-d]pyrimidin-4-yl)piperazine-1-carboximidamide | 400 |
| (S)—N'-cyano-N-(3-isopropylphenyl)-2-methyl-4-(5-methyl-7H-pyrrolo[2,3-d]pyrimidin-4-yl)piperazine-1-carboximidamide | 417.1 |
| (S)—N'-cyano-N-(4-((dimethylamino)methyl)phenyl)-2-methyl-4-(5-methyl-7H-pyrrolo[2,3-d]pyrimidin-4-yl)piperazine-1-carboximidamide | 432.2 |
| (S)—N'-cyano-N-(4-fluoro-3-methylphenyl)-2-methyl-4-(5-methyl-7H-pyrrolo[2,3-d]pyrimidin-4-yl)piperazine-1-carboximidamide | 407.2 |
| (S)—N'-cyano-N-(4-fluorophenyl)-2-methyl-4-(5-methyl-7H-pyrrolo[2,3-d]pyrimidin-4-yl)piperazine-1-carboximidamide | 393 |
| (S)—N'-cyano-N-(4-fluorophenyl)-3-methyl-4-(5-methyl-7H-pyrrolo[2,3-d]pyrimidin-4-yl)piperazine-1-carboximidamide | 393 |
| (S)—N'-cyano-N-(4-methoxyphenyl)-2-methyl-4-(5-methyl-7H-pyrrolo[2,3-d]pyrimidin-4-yl)piperazine-1-carboximidamide | 405 |
| (S)—N'-cyano-N,N-bis(2-hydroxyethyl)-2-methyl-4-(5-methyl-7H-pyrrolo[2,3-d]pyrimidin-4-yl)piperazine-1-carboximidamide | |
| (S)—N'-cyano-N-cyclopropyl-2-methyl-4-(5-methyl-7H-pyrrolo[2,3-d]pyrimidin-4-yl)piperazine-1-carboximidamide | 339 |
| (S)-tert-butyl 3-((S)-N'-cyano-2-methyl-4-(5-methyl-7H-pyrrolo[2,3-d]pyrimidin-4-yl)piperazine-1-carboximidamido)pyrrolidine-1-carboxylate | 468 |
| (S)-tert-butyl 4-(N'-cyano-2-methyl-4-(5-methyl-7H-pyrrolo[2,3-d]pyrimidin-4-yl)piperazine-1-carboximidamido)piperidine-1-carboxylate | 382 |
| [(3-{[(S)-2-Methyl-4-(5-methyl-7H-pyrrolo[2,3-d]pyrimidin-4-yl)-piperazine-1-carbonyl]-amino}-phenylcarbamoyl)-methyl]-carbamic acid tert-butyl ester | 523 |
| 2,5-Dimethyl-4-(5-methyl-7H-pyrrolo[2,3-d]pyrimidin-4-yl)-piperazine-1-carboxylic acid (3-bromo-phenyl)-amide | 445 |
| 2,6-Dimethyl-4-(5-methyl-7H-pyrrolo[2,3-d]pyrimidin-4-yl)-piperazine-1-carboxylic acid (3-bromo-phenyl)-amide | 443; 445 |
| 2,6-Dimethyl-4-(5-methyl-7H-pyrrolo[2,3-d]pyrimidin-4-yl)-piperazine-1-carboxylic acid [3-(4-fluoro-phenoxy)-phenyl]-amide | 475 |
| 2-[3-(4-Fluoro-phenoxy)-phenyl]-1-[4-(5-methyl-7H-pyrrolo[2,3-d]pyrimidin-4-yl)-piperazin-1-yl]-ethanone | 446.1 |
| 2-Methyl-4-(5-methyl-7H-pyrrolo[2,3-d]pyrimidin-4-yl)-piperazine-1-carboxylic acid (3-bromo-phenyl)-amide | 429 |
| 3-({[(E)-Ethanesulfonylimino]-[(S)-2-methyl-4-(5-methyl-7H-pyrrolo[2,3-d]pyrimidin-4-yl)-piperazin-1-yl]-methyl}-amino)-N-isopropyl-benzamide | 527 |
| 3-({[(E)-Ethanesulfonylimino]-[(S)-2-methyl-4-(5-methyl-7H-pyrrolo[2,3-d]pyrimidin-4-yl)-piperazin-1-yl]-methyl}-amino)-benzoic acid methyl ester | 500 |
| 3-({[(E)-Ethanesulfonylimino]-[(S)-2-methyl-4-(5-methyl-7H-pyrrolo[2,3-d]pyrimidin-4-yl)-piperazin-1-yl]-methyl}-amino)-N-pyridin-4-yl-benzamide | 562 |

TABLE 1-continued

| Compound | (M + H)+ |
|---|---|
| 3-({[(E)-Ethanesulfonylimino]-[(S)-2-methyl-4-(5-methyl-7H-pyrrolo[2,3-d]pyrimidin-4-yl)-piperazin-1-yl]-methyl}-amino)-N-ethyl-benzamide | 513 |
| 3-({[(E)-Ethanesulfonylimino]-[(S)-2-methyl-4-(5-methyl-7H-pyrrolo[2,3-d]pyrimidin-4-yl)-piperazin-1-yl]-methyl}-amino)-benzamide | 485 |
| 3-({[(E)-Ethanesulfonylimino]-[(S)-2-methyl-4-(5-methyl-7H-pyrrolo[2,3-d]pyrimidin-4-yl)-piperazin-1-yl]-methyl}-amino)-N-phenyl-benzamide | 561 |
| 3-({[(E)-Ethanesulfonylimino]-[(S)-2-methyl-4-(5-methyl-7H-pyrrolo[2,3-d]pyrimidin-4-yl)-piperazin-1-yl]-methyl}-amino)-N-(1-methyl-piperidin-4-yl)-benzamide | 582 |
| 3-({[(E)-Ethanesulfonylimino]-[(S)-2-methyl-4-(5-methyl-7H-pyrrolo[2,3-d]pyrimidin-4-yl)-piperazin-1-yl]-methyl}-amino)-N-(2-morpholin-4-yl-ethyl)-benzamide | 598 |
| 3-(5-Methyl-7H-pyrrolo[2,3-d]pyrimidin-4-yl)-3,8-diaza-bicyclo[3.2.1]octane-8-carboxylic acid (3-bromo-phenyl)-amide | 442.9 |
| 4-(5-Methyl-7H-pyrrolo[2,3-d]pyrimidin-4-yl)-piperazine-1-carbothioic acid (4-fluoro-phenyl)-amide | 371.2 |
| 4-(5-Methyl-7H-pyrrolo[2,3-d]pyrimidin-4-yl)-piperazine-1-carbothioic acid pyridin-3-ylamide | 354 |
| 4-(5-Methyl-7H-pyrrolo[2,3-d]pyrimidin-4-yl)-piperazine-1-carboxylic acid [3-(4-fluoro-phenoxy)-phenyl]-amide | 447 |
| 4-(5-Methyl-7H-pyrrolo[2,3-d]pyrimidin-4-yl)-piperazine-1-carboxylic acid (3-bromo-4-fluoro-phenyl)-amide | 435 |
| 4-(5-Methyl-7H-pyrrolo[2,3-d]pyrimidin-4-yl)-piperazine-1-carboxylic acid (3-bromo-phenyl)-amide | 417 |
| 4-(5-Methyl-7H-pyrrolo[2,3-d]pyrimidin-4-yl)-piperazine-1-carboxylic acid (3-bromo-phenyl)-amide | 415, 417 |
| 4-(5-Methyl-7H-pyrrolo[2,3-d]pyrimidin-4-yl)-piperazine-1-carboxylic acid (3,4-difluoro-phenyl)-amide | 373.1 |
| 4-(5-Methyl-7H-pyrrolo[2,3-d]pyrimidin-4-yl)-piperazine-1-carboxylic acid (4-fluoro-phenyl)-amide | 355.2 |
| 4-(5-Methyl-7H-pyrrolo[2,3-d]pyrimidin-4-yl)-piperazine-1-carboxylic acid [4-fluoro-3-(4-phenoxy)-phenyl]-amide | 465.1 |
| 4-(5-Methyl-7H-pyrrolo[2,3-d]pyrimidin-4-yl)-piperazine-1-carboxylic acid (3-chloro-2-methyl-phenyl)-amide | 385.2 |
| 4-(5-Methyl-7H-pyrrolo[2,3-d]pyrimidin-4-yl)-piperazine-1-carboxylic acid (3-cyano-phenyl)-amide | 362.2 |
| 4-(5-Methyl-7H-pyrrolo[2,3-d]pyrimidin-4-yl)-piperazine-1-carboxylic acid (2,3-dichloro-phenyl)-amide | 407 |
| 4-(5-Methyl-7H-pyrrolo[2,3-d]pyrimidin-4-yl)-piperazine-1-carboxylic acid (2,3-dimethyl-phenyl)-amide | 365.1 |
| 4-(5-Methyl-7H-pyrrolo[2,3-d]pyrimidin-4-yl)-piperazine-1-carboxylic acid (3-chloro-phenyl)-amide | 371.2 |
| 4-(5-Methyl-7H-pyrrolo[2,3-d]pyrimidin-4-yl)-piperazine-1-carboxylic acid m-tolylamide | 351.2 |
| 4-(5-Methyl-7H-pyrrolo[2,3-d]pyrimidin-4-yl)-piperazine-1-carboxylic acid (3-fluoro-4-methyl-phenyl)-amide | 369 |
| 4-(5-Methyl-7H-pyrrolo[2,3-d]pyrimidin-4-yl)-piperazine-1-carboxylic acid biphenyl-2-ylamide | 413 |
| 4-(5-Methyl-7H-pyrrolo[2,3-d]pyrimidin-4-yl)-piperazine-1-carboxylic acid (3-methylsulfanyl-phenyl)-amide | 383 |
| 4-(5-Methyl-7H-pyrrolo[2,3-d]pyrimidin-4-yl)-piperazine-1-carboxylic acid [2-(1H-indol-3-yl)-ethyl]-amide | 404.2 |
| 4-(5-Methyl-7H-pyrrolo[2,3-d]pyrimidin-4-yl)-piperazine-1-carboxylic acid 3-fluoro-benzylamide | 369 |
| 4-(5-Methyl-7H-pyrrolo[2,3-d]pyrimidin-4-yl)-piperazine-1-carboxylic acid (3,5-dimethoxy-phenyl)-amide | 397.05 |
| 4-(5-Methyl-7H-pyrrolo[2,3-d]pyrimidin-4-yl)-piperazine-1-carboxylic acid (3-methoxy-phenyl)-amide | 367.1 |
| 4-(5-Methyl-7H-pyrrolo[2,3-d]pyrimidin-4-yl)-piperazine-1-carboxylic acid (3-bromo-phenyl)-methyl-amide | 431 |
| 4-[(S)-4-(6-Chloro-5-methyl-pyrimidin-4-yl)-3-methyl-piperazin-1-yl]-5-methyl-7H-pyrrolo[2,3-d]pyrimidine | 358.2 |
| 4-Fluoro-N-(3-{2-[4-(5-methyl-7H-pyrrolo[2,3-d]pyrimidin-4-yl)-piperazin-1-yl]-2-oxo-ethyl}-phenyl)-benzamide | 473.2 |
| Acetic acid 2-(3-{[(S)-2-methyl-4-(5-methyl-7H-pyrrolo[2,3-d]pyrimidin-4-yl)-piperazine-1-carbonyl]-amino}-benzoylamino)-ethyl ester | 480.1 |
| Dimethyl-carbamic acid 3-({[(E)-ethanesulfonylimino]-[(S)-2-methyl-4-(5-methyl-7H-pyrrolo[2,3-d]pyrimidin-4-yl)-piperazin-1-yl]-methyl}-amino)-phenyl ester | 529 |
| Dimethyl-carbamic acid 4-{[(S)-2-methyl-4-(5-methyl-7H-pyrrolo[2,3-d]pyrimidin-4-yl)-piperazine-1-carbonyl]-amino}-phenyl ester | 438 |
| Ethanesulfonic acid 1-(2-methyl-benzooxazol-5-ylamino)-1-[(S)-2-methyl-4-(5-methyl-7H-pyrrolo[2,3-d]pyrimidin-4-yl)-piperazin-1-yl]-meth-(E)-ylideneamide | 497 |
| Ethanesulfonic acid 1-(3-bromo-phenylamino)-1-[(S)-2-methyl-4-(5-methyl-7H-pyrrolo[2,3-d]pyrimidin-4-yl)-piperazin-1-yl]-meth-(E)-ylideneamide | 520, 522 |

TABLE 1-continued

| Compound | (M + H)+ |
|---|---|
| Ethanesulfonic acid 1-(3H-benzoimidazol-5-ylamino)-1-[(S)-2-methyl-4-(5-methyl-7H-pyrrolo[2,3-d]pyrimidin-4-yl)-piperazin-1-yl]-meth-(E)-ylideneamide | 482 |
| Ethanesulfonic acid 1-(4-fluoro-3-methoxy-phenylamino)-1-[(S)-2-methyl-4-(5-methyl-7H-pyrrolo[2,3-d]pyrimidin-4-yl)-piperazin-1-yl]-meth-(E)-ylideneamide | 490 |
| Ethanesulfonic acid 1-(benzo[1,3]dioxol-5-ylamino)-1-[(S)-2-methyl-4-(5-methyl-7H-pyrrolo[2,3-d]pyrimidin-4-yl)-piperazin-1-yl]-meth-(E)-ylideneamide | 486 |
| Ethanesulfonic acid 1-(benzofuran-5-ylamino)-1-[(S)-2-methyl-4-(5-methyl-7H-pyrrolo[2,3-d]pyrimidin-4-yl)-piperazin-1-yl]-meth-(E)-ylideneamide | 482 |
| Ethanesulfonic acid 1-(biphenyl-4-ylamino)-1-[(S)-2-methyl-4-(5-methyl-7H-pyrrolo[2,3-d]pyrimidin-4-yl)-piperazin-1-yl]-meth-(E)-ylideneamide | 518 |
| Ethanesulfonic acid 1-[(S)-2-methyl-4-(5-methyl-7H-pyrrolo[2,3-d]pyrimidin-4-yl)-piperazin-1-yl]-1-(5-methyl-thiazol-2-ylamino)-meth-(E)-ylideneamide | 463 |
| Ethanesulfonic acid 1-[(S)-2-methyl-4-(5-methyl-7H-pyrrolo[2,3-d]pyrimidin-4-yl)-piperazin-1-yl]-1-[3-(pyridin-3-yloxy)-phenylamino]-meth-(E)-ylideneamide | 535 |
| Ethanesulfonic acid 1-[(S)-2-methyl-4-(5-methyl-7H-pyrrolo[2,3-d]pyrimidin-4-yl)-piperazin-1-yl]-1-[3-(morpholine-4-carbonyl)-phenylamino]-meth-(E)-ylideneamide | 555 |
| Ethanesulfonic acid 1-[(S)-2-methyl-4-(5-methyl-7H-pyrrolo[2,3-d]pyrimidin-4-yl)-piperazin-1-yl]-1-(pyridin-3-ylamino)-meth-(E)-ylideneamide | 443 |
| Ethanesulfonic acid 1-[(S)-2-methyl-4-(5-methyl-7H-pyrrolo[2,3-d]pyrimidin-4-yl)-piperazin-1-yl]-1-(thiazol-2-ylamino)-meth-(E)-ylideneamide | 449 |
| Ethanesulfonic acid 1-[(S)-2-methyl-4-(5-methyl-7H-pyrrolo[2,3-d]pyrimidin-4-yl)-piperazin-1-yl]-1-phenylamino-meth-(E)-ylideneamide | 442 |
| Ethanesulfonic acid 1-[(S)-2-methyl-4-(5-methyl-7H-pyrrolo[2,3-d]pyrimidin-4-yl)-piperazin-1-yl]-1-(3-oxazol-5-yl-phenylamino)-meth-(E)-ylideneamide | 509 |
| Ethanesulfonic acid 1-[(S)-2-methyl-4-(5-methyl-7H-pyrrolo[2,3-d]pyrimidin-4-yl)-piperazin-1-yl]-1-[3-(2-methyl-thiazol-4-yl)-phenylamino]-meth-(E)-ylideneamide | 539 |
| Ethanesulfonic acid 1-[(S)-2-methyl-4-(5-methyl-7H-pyrrolo[2,3-d]pyrimidin-4-yl)-piperazin-1-yl]-1-(quinolin-7-ylamino)-meth-(E)-ylideneamide | 493 |
| Ethanesulfonic acid 1-[(S)-2-methyl-4-(5-methyl-7H-pyrrolo[2,3-d]pyrimidin-4-yl)-piperazin-1-yl]-1-(quinoxalin-6-ylamino)-meth-(E)-ylideneamide | 494 |
| Ethanesulfonic acid 1-[(S)-2-methyl-4-(5-methyl-7H-pyrrolo[2,3-d]pyrimidin-4-yl)-piperazin-1-yl]-1-(3-trifluoromethyl-phenylamino)-meth-(E)-ylideneamide | 510 |
| Ethanesulfonic acid 1-[(S)-2-methyl-4-(5-methyl-7H-pyrrolo[2,3-d]pyrimidin-4-yl)-piperazin-1-yl]-1-[4-(3-trifluoromethyl-phenoxy)-phenylamino]-meth-(E)-ylideneamide | 602 |
| Ethanesulfonic acid 1-[(S)-2-methyl-4-(5-methyl-7H-pyrrolo[2,3-d]pyrimidin-4-yl)-piperazin-1-yl]-1-(3,4,5-trimethoxy-phenylamino)-meth-(E)-ylideneamide | 532 |
| Ethanesulfonic acid 1-[(S)-2-methyl-4-(5-methyl-7H-pyrrolo[2,3-d]pyrimidin-4-yl)-piperazin-1-yl]-1-[3-(morpholine-4-sulfonyl)-phenylamino]-meth-(E)-ylideneamide | 591 |
| Ethanesulfonic acid 1-[2-(1H-indol-3-yl)-ethylamino]-1-[(S)-2-methyl-4-(5-methyl-7H-pyrrolo[2,3-d]pyrimidin-4-yl)-piperazin-1-yl]-meth-(E)-ylideneamide | 509 |
| Ethanesulfonic acid 1-[3-(4-fluoro-phenoxy)-phenylamino]-1-[(S)-2-methyl-4-(5-methyl-7H-pyrrolo[2,3-d]pyrimidin-4-yl)-piperazin-1-yl]-meth-(E)-ylideneamide | 552 |
| N-(3-{2-[4-(5-Methyl-7H-pyrrolo[2,3-d]pyrimidin-4-yl)-piperazin-1-yl]-2-oxo-ethyl}-phenyl)-isonicotinamide | 456.2 |
| N-(3-bromophenyl)-2-butyl-N'-cyano-4-(5-methyl-7H-pyrrolo[2,3-d]pyrimidin-4-yl)piperazine-1-carboximidamide | 496 |
| N-(3-Bromo-phenyl)-4-(5-methyl-7H-pyrrolo[2,3-d]pyrimidin-4-yl)-piperazine-1-carboxamidine | 416 |
| N-(3-bromophenyl)-N'-cyano-2-(4-fluorobenzyl)-4-(5-methyl-7H-pyrrolo[2,3-d]pyrimidin-4-yl)piperazine-1-carboximidamide | 548 |
| N-(3-bromophenyl)-N'-cyano-2-ethyl-4-(5-methyl-7H-pyrrolo[2,3-d]pyrimidin-4-yl)piperazine-1-carboximidamide | 468 |
| N-(3-bromophenyl)-N'-cyano-4-(5-methyl-7H-pyrrolo[2,3-d]pyrimidin-4-yl)piperazine-1-carboximidamide | 441 |
| N-(3-bromophenyl)-N'-cyano-5-(5-methyl-7H-pyrrolo[2,3-d]pyrimidin-4-yl)-2,5-diazabicyclo[2.2.1]heptane-2-carboximidamide | 452.9 |
| N-[1-(3-Bromo-phenylamino)-1-[(S)-2-methyl-4-(5-methyl-7H-pyrrolo[2,3-d]pyrimidin-4-yl)-piperazin-1-yl]-meth-(E)-ylidene]-benzenesulfonamide | 568, 570 |
| N-[1-(3-Bromo-phenylamino)-1-[(S)-2-methyl-4-(5-methyl-7H-pyrrolo[2,3-d]pyrimidin-4-yl)-piperazin-1-yl]-meth-(E)-ylidene]-4-methoxy-benzenesulfonamide | 598, 600 |
| N-[1-[(S)-2-Methyl-4-(5-methyl-7H-pyrrolo[2,3-d]pyrimidin-4-yl)-piperazin-1-yl]-1-(5-methyl-thiazol-2-ylamino)-meth-(E)-ylidene]-benzenesulfonamide | 511 |
| N-[1-Ethylamino-1-[(S)-2-methyl-4-(5-methyl-7H-pyrrolo[2,3-d]pyrimidin-4-yl)-piperazin-1-yl]-meth-(E)-ylidene]-benzenesulfonamide | 442 |
| N-[1-Isopropylamino-1-[(S)-2-methyl-4-(5-methyl-7H-pyrrolo[2,3- | 456 |

TABLE 1-continued

| Compound | (M + H)+ |
|---|---|
| d]pyrimidin-4-yl)-piperazin-1-yl]-meth-(E)-ylidene]-benzenesulfonamide | |
| Naphthalene-2-sulfonic acid 1-(3-bromo-phenylamino)-1-[(S)-2-methyl-4-(5-methyl-7H-pyrrolo[2,3-d]pyrimidin-4-yl)-piperazin-1-yl]-meth-(E)-ylideneamide | 618, 620 |
| N'-cyano-2-methyl-4-(5-methyl-7H-pyrrolo[2,3-d]pyrimidin-4-yl)-N-m-tolylpiperazine-1-carboximidamide | 389 |
| N'-cyano-N-(3-(4-fluorophenoxy)phenyl)-4-(5-methyl-7H-pyrrolo[2,3-d]pyrimidin-4-yl)piperazine-1-carboximidamide | 471 |
| N'-cyano-N-(3-cyanophenyl)-2-methyl-4-(5-methyl-7H-pyrrolo[2,3-d]pyrimidin-4-yl)piperazine-1-carboximidamide | 400 |
| N'-cyano-N-(3-methoxyphenyl)-2-methyl-4-(5-methyl-7H-pyrrolo[2,3-d]pyrimidin-4-yl)piperazine-1-carboximidamide | 404 |
| tert-butyl 3-((S)-N'-cyano-2-methyl-4-(5-methyl-7H-pyrrolo[2,3-d]pyrimidin-4-yl)piperazine-1-carboximidamido)piperidine-1-carboxylate | 482 |

6.24. Expression and Purification of LIMK2

LIMK2 was expressed using the BAC-to-BAC® Baculovirus Expression System (Invitrogen). Recombinant baculovirus was made according to the manufacturer's directions as set forth in the instruction manual. Briefly, the plasmids (pFactBac1 or pFastBacHT) carrying the LIMK2 inserts were transformed into MAX efficiency DH10Bac competent E. coli to generate a recombinant bacmid. The DH10Bac E. coli host strain contains a baculovirus shuttle vector (bacmid) with a mini-attTn7 target site and a helper plasmid, and allows generation of a recombinant bacmid following transposition between the mini-Tn7 element on the pFastBac vector and the min-attTn7 target site on the bacmid. The transposition reaction occurs in the presence of transposition proteins supplied by the helper plasmid. Cells were plated and the white colonies picked for bacmid isolation as described in the instruction manual.

The isolated bacmid DNA was transfected into SF9 cells to generate a recombinant baculovirus, and virus was collected five days after transfection. Virus was amplified in T75 flasks at a multiplicity of infection (MOI) of 0.2. The amplified virus was used to infect SF9 cells at a MOI 5 for protein expression.

For small scale purification of the LIMK2 constructs, a 50 ml culture of Sf9 cells infected with the recombinant baculovirus was used. The cells were harvested by centrifugation for 5 minutes at 500×g. The cells were then resuspended in lysis buffer (5 volumes per gram of cells). A typical lysis buffer contains the following: 50 mM HEPES (pH 8.0), 300 mM KCl, 10% glycerol, 1% NP-40, 15 mM imidazole, 1 mM benzamidine, and Roche complete protease inhibitors (1 tablet per 50 ml of cell lysate). The cellular suspension was lysed by one passage through a Microfluidics Microfluidizer M-110Y at a liquid pressure of 14,000 to 20,000 psi followed by centrifugation of the lysate at 60,000×g for 15 minutes at 4° C.

The supernatant was then loaded directly onto a chromatography matrix containing Cobalt ion covalently attached to nitrilotriacetic acid NTA. The chromatography matrix was equilibrated in the same buffer as the protein loading solution. The ion charged resin typically has a binding capacity equivalent to 5 to 10 mg histidine-tagged protein per ml of packed resin. The amount of extract that can be loaded onto the column depends on the amount of soluble histidine-tagged protein in the extract. The column was then washed in a stepwise fashion, first with: 50 mM HEPES (pH 8.0), 300 mM KCl, 10% glycerol, 1% NP-40, 15 mM imidazole, 1 mM benzamidine; second, with 20 mM HEPES (pH 8.0), 500 mM KCl, 10% glycerol, and 20 mM imidazole; third, with 20 mM HEPES (pH 8.0), 100 mM KCl, 10% glycerol, and 20 mM imidazole; followed by elution with 250 mM imidazole in the same buffer. The LIMK2 protein solution was then analyzed by SDS-PAGE and Western blot using commercial antibodies directed to both the carboxyl terminus and internal catalytic domains of the protein. For storage purposes the protein was dialyzed into 50 mM Tris (pH 7.5), 150 mM NaCl, 0.1% BME, 0.03% Brij-35, and 50% glycerol.

Large scale LIMK2 purification was done in a Wave Bioreactor (Wave Biotech) with 10 L culture volumes. 10 L of cell culture at $2\text{-}3\times10^6$ viable cells/mL were infected at an MOI=5 pfu/cell and harvested at 48 hours post infection.

6.25. In Vitro LIMK2 Inhibition Assay

An in vitro assay used to identify LIMK2 inhibitors was developed. The analytical readout was the incorporation of $^{33}P$ from ATP substrate into immobilized myelin basic protein coated flash plates (Perkin Elmer Biosciences), which were counted on a scintillation counter equipped with a plate reader (TopCount, Packard Bioscience, Meriden, Conn.). Using 384 well flat MBP flashplates, total assay volume was 50 µl. The HTS program utilized a Biomek FX for dilution.

For each assay, the ingredients and conditions were as follows: 200 ng of enzyme was incubated in assay buffer (1× assay buffer contains 30 mM HEPES (pH 8.0), 5 mM DTT, and 10 mM $MgCl_2$), 10 µM ATP, 0.2 µCi [gamma-$^{33}P$]-ATP and 10 µM of potential inhibitory compound. The reaction was incubated at room temperature for 60 minutes, washed 3 times with 75 µl of stop/wash buffer (1× stop/was buffer contains 50 mM EDTA and 20 mM Tris (pH 7.4)), and then the plates were read on the scintillation counter. Different concentrations of staurosporine (400 nM, 200 nM, 100 nM and 50 nM; purchased from BIOMOL (Plymouth Meeting, Pa.)) were used as controls on each plate.

6.26. Pig Anterior Chamber Organ Culture Perfusion Assay

Freshly enucleated eyes were obtained from a local slaughter house. Eyes were harvested immediately after death and placed on ice. Anterior chamber dissections were performed within 4 hours after the pig was sacrificed. To prepare the anterior segments for perfusion the eyes were first cleaned by removing all extra-orbital muscles and immersing the orbit in 1% iodine (Veterinary Products Laboratories, Phoenix, Ariz.) for 30 seconds. A circular incision was then made around the posterior circumference of the orbit and this posterior section of sclera including optic nerve is removed and discarded. The vitreous, retina, lens, and choroid were then carefully removed without damaging the outflow angle in the anterior portion of the eye. The inner central ring of the iris was also removed. The clean and dissected anterior chamber was then placed on the perfusion chamber. Unintended leakage from around the eye was eliminated by placing high vacuum grease (Dow Corning Corp., Midland, Mich.) between the distal sclera and perfusion chamber and securing the eye in place with a 4C (5/16") 3 Oz orthodontic rubber band (ORMCO Corp., Glendora, Calif.). Once secured the perfusion set-up is filled with the perfusion media. The perfusion media was DMEM supplemented with 4.5 g/L D-glucose, 200 units/ml penicillin G, 200 μg/ml streptomycin sulfate, and 0.2 mM L-glutamine (Invitrogen, Grand Island, N.Y.). The media-filled perfusion set-up was then connected to the infusion tubing and programmable syringe pump. Pressure was monitored by placing a blood pressure sensor (WPI, Sarasota, Fla.) in-line between the syringe pump and perfusion chamber. The sensor relayed the signal through a Bridge-8 amplifier (WPI, Sarasota, Fla.). The amplified signal was converted to a digital read-out through a MP-100 data acquisition system (WPI. Sarasota, Fla.), and the data was analyzed using the Acq-Knowledge software (WPI. Sarasota, Fla.). Any perfusion chamber set-up that could not maintain a steady pressure due to leaking was removed from the assay.

Once four anterior chamber perfusion set-ups were made, the chambers were allowed to warm to 35° C. for several hours while being perfused with media at a rate of 2 μl/min. Once the perfusion set-ups were stabilized, the first control media exchange of 15 ml was performed. The exchange rate was 5 ml/min. The perfusion set-ups were then allowed to establish an overnight baseline at a flow rate of 2 μl/min. The next morning, a second control media exchange was performed in the same way. This second exchange was used to establish the 2 hour baseline for the compound study. After establishing a 2 hour baseline that does not have more than a 1 mmHg drift, the compound media exchange was performed. Compound media exchanged were performed on two of the four perfusion set-ups. The remaining perfusion set-ups received a vehicle media exchange. All exchanged were performed at a rate of 5 ml/min and an exchange volume of 25 ml. After the exchange, the perfusion set-ups were perfused at a rate of 2 μl/min for at least 4 hr. Outflow facility was calculated by dividing the resultant IOP pressure (mmHg) by the flow rate (μl/min). Data were plotted as a relative difference from time zero, i.e., the time after the 2 hr baseline and before the compound/vehicle exchange.

6.27. Dexamethasone-Induced Ocular Hypertension Model

Twenty eight day mouse Alzet mini-osmotic pumps (DURECT Corp., Cupertino, Calif.) were filled with a solution of water soluble dexamethasone (dex) in PBS (Sigma, St. Louis, Mo.) so that they would release roughly 0.1 mg of dex per day. Once the pumps were filled with the dex, the pumps were allowed to equilibrate in PBS at 37° C. for 60 hours. The equilibrated pumps were surgically placed subcutaneously on the backs of wild-type C57:129 F2 hybrid mice weighing between 25 and 35 grams. Surgical incisions were sutured with 5-0 braided silk (ROBOZ, Gaithersburg, Md.) and treated with antibiotic ointment throughout the entire duration of study. Intraocular pressure (IOP) was measured on these mice using a TonoLab (Colonial Medical Supply Co., Franconia, N.H.) tonometer. Mice were mildly sedated with isoflurane and topically anesthetized with 0.5% proparacaine (Akorn, Buffalo Grove, Ill.) before IOP measurements were taken. Baseline IOP was measured 1 day prior to mini-pump implantation. After mini-pump implantation, IOP measurements were taken 2-3 times per week for 4 weeks. Pharmacology studies with potential ocular hypotensive compounds were performed between 21 and 28 days after implantation.

6.28. In Vivo Effects

Compounds of the invention found to affect conventional outflow in the pig anterior chamber organ culture perfusion assay described above were then tested in the mouse ocular hypertensive model.

As shown in FIG. 1, a 100 μM solution of a compound of the invention significantly increased conventional outflow in the pig perfusion assay as compared to the vehicle control. And as shown in FIG. 2, the topical administration of that same compound significantly lowered intraocular pressure in female F2 wild-type ocular hypertensive mice. The data in this figure were obtained one hour after topical treatment.

All publications (e.g., patents and patent applications) cited above are incorporated herein by reference in their entireties.

What is claimed is:
1. A compound of formula I:

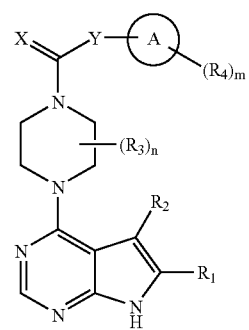

or a pharmaceutically acceptable salt thereof, wherein:
X is O;
Y is O or $NR_B$;
A is aryl;
$R_1$ is hydrogen, $OR_B$, $N(R_B)_2$, $SR_B$, or optionally substituted alkyl, aryl, or heterocycle;
$R_2$ is optionally substituted lower alkyl;
each $R_3$ is independently halogen or optionally substituted alkyl, and/or two $R_3$s may be taken together with the ring to which they are attached to provide an optionally substituted cycloalkyl or heterocyclyl;
each $R_4$ is cyano, halogen, hydroxy, nitro, $R_C$, $OR_C$, $N(R_C)_2$, $NHC(O)R_C$, $C(O)R_C$, $C(O)N(R_C)_2$, or $SO_2R_C$;
each $R_B$ is independently hydrogen or optionally substituted alkyl;
each $R_C$ is independently hydrogen or optionally substituted alkyl, heteroalkyl, aryl, heterocyclyl, alkylaryl, or alkylheterocycle;
n is 0-8; and
m is 0-4.

2. The compound of claim 1, wherein Y is $NR_B$.
3. The compound of claim 1, wherein $R_1$ is hydrogen.
4. The compound of claim 1, wherein $R_2$ is methyl.
5. The compound of claim 1, wherein $R_3$ is optionally substituted lower alkyl.
6. The compound of claim 5, wherein $R_3$ is methyl.
7. The compound of claim 1, wherein $R_4$ is halogen.

8. The compound of claim 7, wherein $R_4$ is bromine or fluorine.

9. The compound of claim 1, wherein $R_4$ is $R_C$.

10. The compound of claim 1, wherein $R_1$ is $C(O)NHR_C$.

11. A compound of formula II:

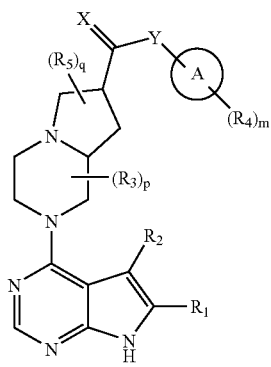

II or a pharmaceutically acceptable salt thereof, wherein:

X is O or $NR_A$;

Y is O, $NR_B$, or $C(R_B)_2$;

A is cycloalkyl, aryl or heterocyclyl;

$R_1$ is hydrogen, $OR_B$, $N(R_B)_2$, $SR_B$, or optionally substituted alkyl, aryl, or heterocyclyl;

$R_2$ is hydrogen, halogen, cyano, $OR_B$, $N(R_B)_2$, $SR_B$, or optionally substituted alkyl, aryl, or heterocyclyl;

each $R_3$ is independently halogen or optionally substituted alkyl, and/or two $R_3$s may be taken together with the ring to which they are attached to provide an optionally substituted cycloalkyl or heterocyclyl;

each $R_4$ is cyano, halogen, hydroxy, nitro, $R_C$, $OR_C$, $N(R_C)_2$, $NHC(O)R_C$, $C(O)R_C$, $C(O)N(R_C)_2$, or $SO_2R_C$;

$R_5$ is oxo;

$R_A$ is hydrogen, cyano, nitro, $R_{A1}$, $SO_2R_{A1}$, $SO_2NR_{A1}$, or $SO_2N(R_{A1})_2$;

each $R_{A1}$ is independently hydrogen or optionally substituted alkyl, heteroalkyl, aryl, heterocyclyl, alkylaryl, or alkylheterocycle;

each $R_B$ is independently hydrogen or optionally substituted alkyl;

each $R_C$ is independently hydrogen or optionally substituted alkyl, heteroalkyl, aryl, heterocyclyl, alkylaryl, or alkylheterocycle;

m is 0-4;

p is 0-3; and q is 0-2.

12. The compound of claim 11, which is of the formula:

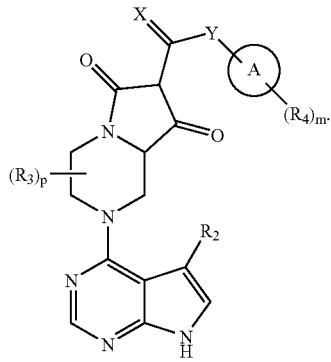

* * * * *